(12) United States Patent
Huijbregts et al.

(10) Patent No.: US 12,357,200 B2
(45) Date of Patent: Jul. 15, 2025

(54) SWEAT SENSOR

(71) Applicant: KONINKLIJKE PHILIPS N.V., Eindhoven (NL)

(72) Inventors: Laurentia Johanna Huijbregts, Eindhoven (NL); Frank Mueller, Oosterhout (NL); Lutz Christian Gerhardt, Noord-Brabant (NL); Kiran Hamilton J. Dellimore, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 465 days.

(21) Appl. No.: 17/917,106

(22) PCT Filed: Apr. 1, 2021

(86) PCT No.: PCT/EP2021/058567
§ 371 (c)(1),
(2) Date: Oct. 5, 2022

(87) PCT Pub. No.: WO2021/209267
PCT Pub. Date: Oct. 21, 2021

(65) Prior Publication Data
US 2023/0148915 A1    May 18, 2023

(30) Foreign Application Priority Data

Apr. 15, 2020 (EP) .................... 20169661

(51) Int. Cl.
*A61B 5/145* (2006.01)
*A61B 5/00* (2006.01)

(52) U.S. Cl.
CPC ........ *A61B 5/14517* (2013.01); *A61B 5/4266* (2013.01)

(58) Field of Classification Search
CPC .................... A61B 5/14517; A61B 5/4266
See application file for complete search history.

(56) References Cited

U.S. PATENT DOCUMENTS

| 2015/0011216 A1 | 1/2015 | Jung |
| 2018/0020966 A1 | 1/2018 | Begtrup |
| 2018/0042585 A1 | 2/2018 | Heikenfeld |

FOREIGN PATENT DOCUMENTS

| EP | 18200903 A1 | 4/2020 |
| EP | 19194586 A1 | 3/2021 |

(Continued)

OTHER PUBLICATIONS

Gao et al. in "Fully integrated wearable sensor arrays for multiplexed in situ perspiration analysis", Nature 529, 509-514 (2016).

(Continued)

*Primary Examiner* — Scott Luan

(57) ABSTRACT

The present invention relates to devices and methods for uptaking and analyzing sweat from a skin of a user. In particular, it is proposed to provide a variability in the size of the sweat sensor inlets (102, 103, 104), which can be used for improving the determination of sweat parameters like for example determining the number of active sweat glands The variability in the size of the inlets (102, 103, 104) with which the sweat sensor (100) uptakes the sweat from the user's skin (111) can be achieved by having either plurality of inlets wherein at least some of them have different opening sizes and to use the differently sized inlets based in different situations. Alternatively, one or more inlets may have openings with variable cross-sectional area, like e.g. an adjustable diameter of their opening, and also a combination of these two alternatives is of course possible. A processor of the sweat sensor may use the information from either all or only the most appropriate sized inlets to determine a sweat parameter. In another alternative, the processor may adapt the inlet to the adjustable inlet opening to the most appropriate size to then determine a sweat parameter of interest.

13 Claims, 6 Drawing Sheets

(56) References Cited

FOREIGN PATENT DOCUMENTS

| WO | 2010023596 A1 | 3/2010 |
|---|---|---|
| WO | 2018125695 A1 | 7/2018 |
| WO | 2019183529 A1 | 9/2019 |
| WO | 2020187875 A1 | 9/2020 |

OTHER PUBLICATIONS

Taylor in "Regional variations in transepidermal water loss, eccrine sweat gland density, sweat secretion rates and electrolyte composition in resting and exercising humans", Extrem Physiol Med 2013; 2:4.

Chen et al: "A Capillary-Evaporation Micropump for Real-Time Sweat Rate Monitoring with and Electrochemical Sensor", Micromachines (Basel) Jul. 10, 2019(7): 457.

Heikenfeld et al., in "Digital nanoliter to milliliter flow rate sensor with in vivo demonstration for continuous sweat rate measurement", Lab Chip, 2019,19, 178.

Yang et al. in "Wearable microfluidics: fabric-based digital droplet flowmetry for perspiration analysis", Lab on a Chip. Accepted Jan. 4, 2017. DOI: 10.1039/c6lc01522k.

Seo Gyun Kim et al. "Human-Iris-Like Aperture and Sphincter Muscle Comprising Hyperelastic composite Hydrogels Containing Graphene Oxide", Macromol. Mater. Eng. 2019, 304, 1800560.

Z. Sonner et al. "The microfluidics of the eccrine sweat gland, including biomarker partitioning, transport, and biosensing implications" published in Biomicrofluidics 9, 031301.

Yuji Gao et al: "Wearable Devices: Wearable Microfluidic Diaphragm Pressure Sensor for Health and Tactile Touch Monitoring (Adv. Mater. 39/2017)", Advanced Materials, Oct. 18, 2017.

International Search Report for International Appln: PCT/2021/058567 Filed Apr. 1, 2021, Dated May 21, 2021.

https://www.newport.com/f/optical-iris-diaphragms.

Jessica Francis, Isaac Stamper, Jason Heikenfeld, and Eliot F. Gomez, "Digital nanoliter to milliliter flow rate sensor with in vivo demonstration for continuous sweat rate measurement", Lab Chip, 2019, 19, 178.

O. Bar-Or, H.M. Lundegren, L.I. Magnusson, E.R. Buskirk, "Distribution of heat-activated sweat glands in obese and lean men and women", Hum Biol. May 1968;40(2):235-48.

W.L. Kenney, "A review of comparative responses of men and women to heat stress", Environmental Research 37, 1-11 (1985).

M.J. Buono and K.P. Connolly, "Increases in swat rate during exercise: gland recruitment versus output per gland", J. therm. Biol. vol. 17, pp. 267-270 (1992).

D. Gagnon and G.P. Kenny, "Sex differences in thermoeffector responses during exercise at fixed requirements for heat loss", J Appl Physiol 113: 746-757 (2012).

Phillip Simmers, S. Kevin Li, Gerald Kasting, and Jason Heikenfeld, "Prolonged and localized sweat stimulation by iontophoretic delivery of the slowly-metabolized cholinergic agent carbachol", Journal of Dermatological Science 89 (2018) 40-51.

Miek Messerschmidt "On compact packings of the plane with circles of three radii," Computational Geometry 86 (2020) 101564. 10.1016/j.comgeo.2019.05.002. https://www.researchgate.net/figure/A-compact-circle-packing-P-with-radiiP-s-0-r-0-1-where-s-0-0208266-and-r_fig2_319642756.

Borkovec, Michal & De Paris, Walter & Peikert, Ronald "The Fractal Dimension of the Apollonian Sphere Packing," Fractals 2, p. 521-526 (1994). 10.1142/S0218348X94000739. https://www.researchgate.net/figure/The-2-dimensional-Apollonian-packing-Dotted-lines-represent-the-inversion-circles_fig1_228326605.

Koh et al: "A soft wearable microfluidic device for the apture, storage, and colorimetric sensing of sweat", Science Translational Medicine 8, (2016), Nov. 23, 2016, pp. 1-13.

SWEAT SENSOR

CROSS-REFERENCE TO PRIOR APPLICATIONS

This application is the U.S. National Phase application under 35 U.S.C. § 371 of International Application No. PCT/EP2021/058567 filed on Apr. 1, 2021, which claims the benefit of European Application No. 20169661.4 filed on Apr. 15, 2020. These applications are hereby incorporated by reference herein.

FIELD OF THE INVENTION

The present invention relates to sweat analysis by wearable sensors. In particular, the present invention relates to a sweat sensor for analyzing a user's sweat uptaken from a user's skin into the sweat sensor, to a method of analyzing the user's sweat uptaken by a sensor from the user's skin and to a computer program element.

BACKGROUND OF THE INVENTION

Non-invasive, semi-continuous and prolonged monitoring of biomarkers, i.e. biomolecules, that indicate disease/health status and well-being is in demand for monitoring, for example, dehydration, stress, sleep, children's health and in perioperative monitoring.

Sweat, tear fluid and saliva may all be obtained non-invasively. Sweat is a particularly accessible biofluid, and is a rich source of information relating to the physiology and metabolism of a subject.

Some examples of clinical relevant components of sweat are $Na^+$, $Cl^-$ and/or $K^+$ to monitor dehydration, lactate as an early warning for inflammation (which is relevant to sepsis), glucose for diabetics and neonates, and cortisol in relation to sleep apnoea and stress monitoring.

Continuous monitoring of high-risk patients, such as those with serious chronic conditions, pre- or post-operative patients, and the elderly, using sweat biomarker monitoring devices can provide higher quality diagnostic information than regular biomarker spot checks as normally done by repeatedly drawing multiple blood samples. Such continuous monitoring may be in a hospital setting or elsewhere. Human sweat alone or as mixture with sebum lipids may be an easily accessible source for biomarker measurements in wearable on-skin devices. For instance, cholesterol is an important biomarker associated with elevated risk in development of cardiovascular diseases. Inflammatory markers or cytokines, such as interleukins (e.g. TNF-a, IL-6) play an important role in the immune response and detection or disease monitoring of joint damage in rheumatoid and psoriatic arthritis, and bowel disease.

Examples of biomarkers/biomolecules that can be detected in eccrine/apocrine sweat using suitable capture species (antibodies, aptamers, molecular imprint polymers, etc.) are: small molecules such as urea, creatinine, cholesterol, triglycerides, steroid hormones (cortisol), glucose, melatonin; peptides and proteins, including cytokines such as IL-1alpha, IL-1beta, IL-6, TNF alpha, IL-8 and TGF-beta IL-6, Cysteine proteinases, DNAse I, lysozyme, Zn-α2-glycoprotein, cysteine-rich secretory protein-3 and Dermcidin; and large biomarkers such as the Hepatitis C virus.

As summarized by Mena-Bravo and de Castro in "Sweat: A sample with limited present applications and promising future in metabolomics", J. Pharm. Biomed. Anal. 90, 139-147 (2014), it has been found that the results from sweat sensing can be highly variable, and a correlation between values determined from blood and sweat samples appears to be lacking for various biomarkers. In this respect, historical studies in this area have involved relatively crude sampling techniques, such as collecting large sweat volumes in bags or textiles. Deficiencies in such techniques may have been a contributing factor to this apparent lack of correlation. The review of Mena-Bravo and de Castro thus highlights further key frustrations with conventional sweat sensing techniques in terms of the difficulty of producing enough sweat for analysis, the issue of sample evaporation, the lack of appropriate sampling devices, the need for trained staff, and issues relating to the normalization of the sampled volume.

Efforts have been made to address these issues by bringing wearable sensors into nearly immediate contact with sweat as it emerges from the skin. A recent example is the wearable patch presented by Gao et al. in "Fully integrated wearable sensor arrays for multiplexed in situ perspiration analysis", Nature 529, 509-514 (2016). The patch includes a sensor array for measuring $Na^+$, $K^+$, glucose, lactate, and skin temperature. However, the focus of this study is on the development and the integration of the sensors themselves which, whilst evidently crucial, does not address issues relating to sweat sample collection. The latter is mostly done by placing a several $cm^2$ sized absorbent pad between the skin and the sensor. The assumption is that, providing ample sweat is produced (hence, tests are carried out on individuals that are exercising), the pad will absorb the sweat for analysis, and newly generated sweat will refill the pad and "rinse away" the old sweat. It is, however, likely that the time-dependent response of the sensor does not directly reflect the actual level of biomarkers over time because of accumulation effects. The sample collection and presentation to the published sensors may not be well-controlled so that continuous reliable sensing over a long period of time is difficult. Such patches may also not be designed to handle the tiny amounts of sweat that are produced under normal conditions, i.e. in the order of subnanoliters to nanoliters per minute per sweat gland.

Adult humans produce heat in the order of 100 Joules per second (100 Watt) when at rest. For a person wearing clothes at a temperature of around 22° C., this heat is removed by passive means such as losing heat by conduction and convection. In this case, the core temperature remains constant. However, when i) a person engages in physical labor or exercise and/or ii) the ambient temperature is increased, such conduction/convection processes are insufficient to maintain the core temperature. To maintain homeostasis, the body induces dilation of blood vessels in the skin to cool the blood, and starts to produce sweat which by evaporation cools the skin.

The amount of sweat produced by persons at ambient temperature with only light exercise or light labor is relatively small as discussed by Taylor in "Regional variations in transepidermal water loss, eccrine sweat gland density, sweat secretion rates and electrolyte composition in resting and exercising humans", Extrem Physiol Med 2013; 2:4, and Simmers in "Prolonged and localized sweat stimulation by iontophoretic delivery of the slowly-metabolised cholinergic agent carbachol", Journal of Dermatological Science 89 (2018) 40-51". In the so-called thermal neutral zone, which is about in the range of 25° C. to 30° C., the core temperature remains very stable and inducing sweat production is not required for cooling down the body. This zone is defined for a naked man at rest. For a person in a resting state wearing clothes, the thermal neutral zone is lower: in the range of about 13° C. to 22° C. Hence, when the temperature is in this zone and the person is in a resting state, the sweat production is very low.

According to Taylor, in resting and thermal neutral conditions, the sympathetic discharge (secretion by the coil of the sweat gland) may not elicit measurable sweating since sweat reabsorption may match its formation rate. Simmers measured the sweat production rates of persons that were wearing clothes, being exposed to an air-conditioned environment, doing primarily non-manual labor and found sweat rates with a typical value of about 0.3 nl/min/gland (values measured between zero and 0.7 nl/min/gland). When persons are at rest but at an elevated temperature of 36° C., a sweat production rate was measured by Taylor to be, on average, $0.36 \text{ mg} \cdot \text{cm}^{-2} \cdot \text{min}^{-1}$. When assuming 2.03 million sweat glands per 1.8 m$^2$ (skin area of an average person) and sweat density of 1 g/ml, the average sweat production is about 3.2 nl/min/gland. Due to the elevated temperature above the thermal neutral zone the body requires cooling and indeed the sweat production rate is increased.

Accordingly, persons in a sedentary state, such as hospital patients, have a minimal sweat rate and there is therefore a significant delay between sweat excretion and biomarker detection, which can prevent timely monitoring and early warning of any impending complication. The concentration of particular relevant biomarkers is sweat rate dependent and therefore the sweat rate per gland should be assessed for a clinically relevant interpretation. Conventional sweat sensing solutions have limited application since they require the monitored person to be engaged in exercise, and tend to use rather complex microfluidics and sensors to determine the sweat rate.

For example, WO 2018/125695 A1 discloses wearable sweat biosensing devices with active sweat sampling. An active method is described for transporting sweat, which utilises the electromechanical effect of electrowetting. Electrowetting plates comprise a hydrophobic dielectric layer (e.g., Teflon) covering electrodes. A sweat coupling "wicking" component made of a hydrophilic material permits sweat from the skin surface to slowly diffuse over time to the electrowetting plates, whereupon the sweat is transported via the electromechanical effect. This approach is very time consuming, and may be ineffective for small sweat volumes due to evaporation. Moreover, the technique entails mixing of sweat received from the skin at different times, which is undesirable for reliable semi-continuous biomarker measurements.

Determining the sweat rate of a user with a sensor is known in the prior art. For example, US 2015/0112165 A1 discloses a method to determine the sweat rate per gland. The method involves using numerous sweat rate sensors to monitor a cumulative change in dielectric value of a porous material in respective sweat collecting chambers. Sodium sensors each monitor the sodium concentration of the sweat in the respective chambers. By use of a correlation curve derived from a volunteer test, the sodium ion concentration is correlated with total sweat flow rate. This approach has two major drawbacks: (i) it assumes a number of sweat glands per surface area during the volunteer test, and (ii) it assumes that the correlation of sodium concentration and sweat rate as determined by the volunteer test is applicable to any particular person/patient. The rather large differences observed between individuals can make the latter assumption unwise, and illness can make such differences even greater.

Heikenfeld et al., in "Digital nanoliter to milliliter flow rate sensor with in vivo demonstration for continuous sweat rate measurement", Lab Chip, 2019,19, 178, and Yang et al. in "Wearable microfluidics: fabric-based digital droplet flowmetry for perspiration analysis", Lab on a Chip. Accepted 4th January 2017. DOI: 10.1039/c6lc01522k, disclose sweat rate sensors, which collect sweat within a chamber positioned adjacent the skin. A sweat droplet grows from an outlet of the chamber until it is released from the outlet by contacting and being transferred to a wick opposing the outlet. Immediately prior to this release, the sweat droplet contacts one of a pair of electrodes, which electrode is mounted on the wick. The other electrode is mounted in the chamber. The electrodes are thus shorted by the connection provided by the sweat in the chamber and the sweat droplet which is still attached thereto. This shorting of the electrodes immediately prior to release of the sweat droplet into the wick enables the device to count the sweat droplets. The design nevertheless necessitates provision of a sweat rate sensor per chamber. This makes the arrangement disadvantageously complex. Moreover, the design may be incompatible with the provision of alternative sweat droplet sensing principles.

SUMMARY OF THE INVENTION

The inventors of the present invention have surprisingly found out that the accuracy of prior art sensors and methods is low for certain sweat rate ranges. The inventors of the present invention have found that this may limit accuracy of the sweat measurements, as will be explained in more detail hereinafter.

It is thus, inter alia, an object of the present invention to provide for an improved sweat sensor and method of analyzing a user's sweat.

The object of the present invention is solved by the subject-matter of the independent claims. Further embodiments and advantages of the invention are incorporated in the dependent claims. Furthermore, it shall be noted that all embodiments of the present invention concerning a method might be carried out with the order of the steps as described, nevertheless this has not to be the only and essential order of the steps of the method as presented herein. The method disclosed herein can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to a first aspect of the present invention, a sweat sensor for analyzing a user's sweat uptaken from a user's skin into the sweat sensor is presented. The sensor comprises one or more inlets through which the user's sweat can be uptaken into the sensor. Furthermore, the sensor comprises an analyzer, which may comprise one or more analyzing units, configured for analyzing the sweat, which was uptaken by the sensor through the one or more inlets. The sensor is configured for controlling a size of an opening of the one or more inlets by either a) changing a cross-sectional area of the opening of the one or more inlets, and/or by b) selecting inlets with a particular size, e.g. to be used for the next analytical cycle of the sensor.

The sensor, and in particular the analyzer, may use or comprise e.g. a processor or a microcontroller for carrying out such a control and/or selection, as will be explained in more detail hereinafter. In some embodiments, the microcontroller of the sensor comprises the processor.

Hence, a sweat sensor is presented comprising various sized inlets and/or one or more size adjustable inlets. Corresponding methods for selecting such various sized inlets and/or methods for controlling, i.e. adjusting, the size of the opening of such inlets with an adjustable opening cross sectional area or diameter will be explained in more detail later on. In other words, the sweat sensor of the present invention is capable of providing at least two sizes of inlets, either by providing one or more inlets with an adjustable opening size and/or by providing at least two distinct inlets with different, pre-determined/fixed sizes, which can be selected/activated in the sense that the sweat uptaken by only the selected inlet or inlets is used for the analysis of the sweat in the next analysis cycle.

The sweat sensor of the present invention can thus react on a determination/measurement of e.g. the sweat rate or the number of sweat glands per inlet by adapting the size of the opening of the inlets that will be used in the next analytical cycle of the sensor. If the sensor has for example determined that the user has a sweat rate that is above a pre-defined threshold value, the sensor can decrease the size of the openings of the inlets, which he will use for next measurements. Such a decrease of the size can then be realized by selecting smaller sized inlets with a corresponding control signal, and/or by adjusting the size of the cross sectional area or diameter of the opening of one or more size adjustable inlets.

The sweat sensor presented herein has a particular advantage when biomolecule (e.g. lactate or e.g. any of the previously mentioned biomolecules) concentrations in sweat are translated back to the concentrations in blood. Such a sweat monitoring provides an optimized method for unobtrusive monitoring of a user, like e.g. a patient or also a healthy human being or an animal. It is known that the correlation between sweat concentrations and blood concentrations depends on the sweat rate per gland, which can be determined by the sensor of the present invention. To determine the sweat rate per gland, the sensor determines the number of active sweat glands. This number not only depends on the person and body location, but may also vary in time. The inventors of the present invention have found that prior art sweat sensors measuring the sweat rate per gland are only accurately measuring for a certain range of active sweat glands per inlet, i.e. surface area. Based on this insight, the present invention increases this range by using inlets of various sizes. In addition, sensors and methods are presented which are configured to execute either an adaptive selection or a dynamic adaptation of these inlets of various sizes, i.e., dynamic range of active sweat glands per inlet/surface area, are described, using preferably the sweat rate of the user to trigger a corresponding control signal. Due to the appropriate size setting for the opening of the inlets used by the sensor, the measurement results of the sensor, e.g. a concentration of a biomolecule in the user's blood, are more accurate than in the prior art.

In preferred embodiments, the sweat rate is determined by means of measuring fluid flow of the uptaken sweat, galvanic skin response (GSR), and/or osmolality, as will be explained in detail hereinafter.

In a preferred embodiment, the sensor controls the size to the appropriate inlet size as described before. Then the one or more analyzing units measure the sweat rate with the correctly sized inlet openings, determine the number of glands and determine the sweat rate per gland. For example, one or more of the discretization methods can be used for such measurements/determinations, which will be described later on in more detail. The one or more analyzing units also measure/determine the concentration of a biomolecule in the uptaken sweat of the user. The sensor is configured for estimating a concentration of the biomolecule in blood of the user based on the determined sweat rate per gland and based on the measured concentration of the biomolecule in the uptaken sweat. Due to the appropriate size setting for the opening of the inlets used by the sensor, the overall measurement results of the sensor, in particular the final estimation of the concentration of the biomolecule in the user's blood, are more accurate as compared to the prior art.

The sweat sensor is thus capable of determining the size of the openings of the inlets, which the sensor uses in the next analytical cycle for uptaking the sweat and also for analyzing the uptaken sweat. As will become apparent from the following detailed description, the sensor can have one or more inlets that can vary in its opening size by means of for example a mechanically controlled diaphragm or a (mechanically) responsive material based aperture. Embodiments of such responsive material based aperture may use e.g. electroactive polymers, magnetorheological elastomer or shape memory polymers or any other suitable stimulus-responsive material. The sensor may in addition or alternatively also have a plurality of inlets, which differ in size and the sensor can control/select, based on a desired target size of the opening of the inlet, which of the differently sized inlets will be used for the next analytical cycle of the sensor. In this next analytical cycle, the sensor will then uptake and analyse sweat only from those inlets, which were accordingly selected by the sensor. In other words, the sweat sensor has various sized inlets and carries out a method for selecting the size of the opening of one or more inlets to be used. The sensor may use e.g. a processor or a microcontroller for carrying out such a control/selection, as will be explained in more detail in the context of e.g. the embodiment of FIG. 5. It should be noted that in the context of the present invention, the described method steps can be carried out by e.g. by a processor and/or a microcontroller of the sweat sensor disclosed herein. In a particular embodiment, the microcontroller described herein comprises the processor.

The sensor may be configured to carry out the controlling, i.e. selecting and/or adjusting, the size of the openings of the inlets, which the sensor will then use in the next analytical cycle, based on e.g. a sweat parameter that has been determined/measured by the sensor in a previous analytical cycle of the sensor. For example, the sensor may determine in a first analytical cycle a sweat rate of the user and depending on the determined value of the sweat rate of the user, the sensor may control, i.e. select and/or adjust, the size of the opening of the one or more inlets, which the sensor will then use for uptaking the sweat and for analyzing the uptaken sweat in the next analytical cycle. However, also other sweat parameters may be determined by the sweat sensor in other embodiments of the present invention, as will be described in more detail hereinafter.

The inventors of the present invention have found that it may be disadvantageous when prior art sweat sensors and methods use inlets that all have the same size and also have a fixed size. The inventors of the present invention have found that prior art sensors, in which all inlets have the same fixed size, may have a limited accuracy in their measurements. This is the case for example when a discretization method is used by the sensor, which will be explained in more detail hereinafter. In particular, if more than a certain number of active sweat glands per inlet are present, measurements of the associated sweat may lose in accuracy. Based on this insight, the present invention provides a sweat sensor, which can control, i.e. select and/or adjust, the size of the opening of at least one inlet of the sensor, e.g. by changing for example a cross sectional area or diameter of the inlet based on a diaphragm mechanism or a radially varying aperture, and/or by actively selecting inlets with a desired size out of a plurality of inlets that have different sizes. A non-limiting example of a sensor with different sized inlets can be gathered from for example the embodiment shown in FIGS. 1 and 2, whereas the embodiments of FIGS. 3 and 4 show different embodiments of a sweat sensor using an inlet with an opening that is adjustable in its cross sectional area or diameter by the sensor via the controlling as described hereinbefore.

It should be noted that the sweat sensor may have only one inlet which is adjustable in the size of the opening, as was just described before for the particular embodiments shown in FIGS. 3 and 4. The sensor may also have at least two differently sized inlets with different sized openings and these two embodiments can of course be combined and can be also upscaled to more inlets with either an adjustable cross sectional areas/diameters or with a large plurality of differently sized openings of the inlets as can be gathered for example from FIG. 2.

With the sweat sensor of the present invention, the sweat may be transported from the skin up into the sensor via for example cylindrical shaped channels and thus the inlets may have a circular shape, as exemplarily shown in FIG. 2. Nevertheless, the present invention does not exclude other shapes/geometries like for example squared inlets or inlets with a triangle shaped cross section. As can be gathered from FIG. 2, the plurality of inlets with different sizes may be provided such that only little void space between the inlets occurs, which is desired in order to keep the sensor small, and making it less obtrusive for the wearer, i.e. the user.

It should be noted that the term "analyzing unit" is to be understood broadly in the context of the present invention. It shall comprise any device that is capable of analyzing the sweat uptaken by the sensor by carrying out a measurement on the sweat. In particular, the analyzing unit may be configured for determining a sweat parameter like for example the sweat rate or the number of active sweat glands per inlet, as will be described hereinafter in more detail. For example, an analyzing unit of the present invention may comprise a fluid flow sensor, or a GSR sensor, or an electrochemical sensor. Of course, prior art devices and methods may be used for implementing such an analyzing unit as is clear to the skilled reader.

Moreover, it should be noted that the term "user" as disclosed herein shall be understood to comprise human beings as well as animals. Thus, the sweat sensor as well as the method of the present invention cannot only be applied for human beings, but also for animals. In particular, livestock monitoring is a valuable application of the present invention.

It should be noted that in the context of the present invention the term "size of the opening of an inlet" describes the cross-sectional area of the opening of the inlet. It is thus the cross-sectional area of the opening of the inlet that is projected onto the skin, as is clear from e.g. the embodiments described for FIGS. 1, 3 and 4. The skilled reader will thus understand this feature as the skin contacting area of the inlet. Instead of cross-sectional area of the opening we will also refer thereto hereinafter as area.

The sweat sensor may comprise not only one analyzing unit, but may comprise a plurality of analyzing units. In a preferred embodiment, for each different inlet of the sensor, a separate analyzing unit is provided, as can be gathered from e.g. the different embodiments of FIGS. 1 and 5.

As will become apparent to the skilled reader from this disclosure, the sweat sensor is a wearable sensor that can be carried by the user in his/her daily life, as several ways for providing an unobtrusive sensor for the wearer are presented herein.

Thus, in a preferred embodiment, the sweat sensor of the present invention comprises a processor or microcontroller, which is configured for controlling the size of the opening of the one or more inlets, which the sensor uses for uptaking the sweat and for analyzing the uptaken sweat, by changing the cross-sectional area of the opening of the one or more inlets, and/or by selecting inlets with a particular size, as was described hereinbefore and will be described hereinafter. Thus, in this embodiment it is the processor or microcontroller of the sweat sensor which carries out the cotrolling.

In a preferred embodiment, the sensor regularly checks, e.g. every second, minute or half an hour, if the size of the inlets is still appropriate or should be changed because the number of active sweat glands, the sweat gland density or the sweat rate has changed considerably. Instead of using a fixed time lapse for that, a trigger like increase/decrease of heart rate or galvanic skin conductance could be used.

According to another embodiment, the sweat sensor, preferably by means of a processor or microcontroller, is configured for:

determining a number of active sweat glands per inlet from which the sweat is uptaken by the sensor, comparing the determined number of active sweat glands per inlet with a reference setting regarding the number of active sweat glands per inlet, wherein the sweat sensor is configured for controlling the size by:

A) increasing the size of the opening of the at least one inlet and/or by selecting one or more inlets with a larger opening for the next analysis cycle as compared to the size of the opening of the one or more inlets that were used in the previous analysis cycle when the determined number of active sweat glands per inlet is below a pre-defined minimum number of active sweat glands per inlet defined in the reference setting, and/or B) decreasing the size of the opening of the at least one inlet and/or by selecting one or more inlets with a smaller opening for the next analysis cycle as compared to the size of the opening of the one or more inlets that were used in the previous analysis cycle when the determined number of active sweat glands per inlet is above a pre-defined maximum number of active sweat glands per inlet defined in the reference setting.

Further details about this embodiment will be elucidated hereinafter.

According to an exemplary embodiment, the one or more analyzing unit is/are configured for determining a sweat parameter of the user by analyzing the uptaken sweat. Moreover, the sensor is configured for controlling the size of the opening of the one or more inlets, which the sensor uses for uptaking the sweat and for analyzing the uptaken sweat, based on the sweat parameter determined by the one or more analyzing units.

Examples of the sweat parameter determined by the analyzing unit are the sweat rate of the user and the number of active sweat glands per inlet/area. Different embodiments of how to determine the parameters will be described in detail hereinafter.

In case a plurality of analyzing units is provided by the sweat sensor, it should be noted that each analyzing unit, for example each analyzing unit that is provided for each inlet of the sensor respectively, is configured to determine the sweat parameter like for example the sweat rate or the number of active sweat glands per corresponding inlet. As a non-limiting example, it is referred to the sensor shown in FIG. 1 comprising the analyzing units 108, 109 and 110, each of which is configured to measure the sweat rate of the user based on the sweat that is uptaken by the corresponding inlet.

In the following, an example is provided in which the one or more analyzing units of the sensor are configured for determining the number of active sweat glands per inlet and the sensor is configured for controlling and thus selecting the size of the one or more inlets which the sensor uses for uptaking the sweat and for analyzing the uptaken sweat in the next analytical cycle of the sensor. Three sizes of inlets are a very practical implementation of the embodiment presented herein. The three sizes could be for example 0.005 $cm^2$, 0.02 $cm^2$ and 0.1 $cm^2$, which, when circular inlets are used, correspond to radii of 0.4 mm, 0.8 mmm and 2 mm, respectively.

As will be appreciated by the skilled person, determining the most appropriate size of the opening of the inlets to be used by the sensor can be based on the determined number of active sweat glands per inlet determined before by the sensor with a respective measurement. If most of the smallest inlets give 0 active sweat glands per inlet (e.g. on average 0.09 active sweat glands per inlet for the smallest inlets), most of the intermediate inlets give 1 or 2 active sweat glands per inlet (e.g. on average 1.5 active sweat glands per inlet for the intermediate inlets), and the largest inlets give 10 or more active sweat glands per inlet (which is a number that, because it is so large, can then not be trusted any more), then the sensor selects the intermediate inlets to have the most appropriate size, since a reference setting stored e.g. within the sensor defines that measurements with more than 5 active sweat glands are not accurate enough. Thus, the sensor sends a corresponding control signal to select only the inlets or to activate only the analyzing units of the inlets of the intermediate size for the next analytical cycle, in which then only sweat from the elected/activated inlets will be used for the next measurement of the uptake sweat. The next measurement, i.e. the measurement in the subsequent analytical cycle, may again be the determination of the number of active sweat glands per inlet, but this measurement may also determine another parameter of the uptaken sweat.

Therefore, the sensor is configured based on the determined sweat parameter of the active sweat glands per inlet to select the intermediate sized inlets for the next analytical cycle. This means that the sensor will only analyze the uptaken sweat that is uptaken by inlets with this intermediate size. Accordingly, the sensor or a processor that might be comprised by the sensor, does not process the data, which originate from inlets with another size than the one that has been determined to be appropriate. Thus, only the inlets with the most appropriate size are used for the next analytical cycle and the sensor can control this accordingly by either adjusting the size of the cross sectional area or the diameter of an opening of the sensor and/or by either not generating analysis data from sweat uptaken by inlets with a non-appropriate size or by neglecting the data that was may be generated by an analyzing unit that corresponds to an inlet with a non-appropriate size.

As the area of the inlets, here of the three different sizes, is generally known, also an active sweat gland density can be calculated by the sweat sensor, if needed. Such a density would be defined as the number of active sweat glands divided by the area.

As will be explained in the context of another embodiment hereinafter, the one or more analyzing unit is configured for measuring a concentration of a biomolecule in the uptaken sweat of the user and in the example described before, the sensor would determine the concentration of the biomolecule only based on the sweat coming from the inlets having the appropriate, intermediate size.

Another exemplary way of determining the most appropriate sized inlets for determining the number of active sweat glands is by using a measured sweat rate, as the sweat rate is correlated with the number of active sweat glands. For example, when the sweat rate is below 5 $nl/min/cm^2$, then the largest inlets are used, when the sweat rate is between 5 and a 100 $nl/min/cm^2$, the intermediate inlets are used, and when the sweat rate is higher than a 100 $nl/min/cm^3$, the smallest inlets are used. The sweat sensor can thus in this example determine the sweat rate with the analyzing units provided and can accordingly control the size of the openings of the inlets which are used for uptaking the sweat and for analyzing the uptaken sweat in the next analytical cycle.

In another example, time varying inlet sizes can be used as follows. Instead of inlets that have a fixed size, inlets can be used that adapt their size in order to get an appropriate size for the determined number of active sweat glands per inlet or for the determined current active sweat gland density. Similar to what was explained before, the appropriate size can be based on the number of active sweat glands determined by the sensor in a previous analytical cycle. For example, when there are per inlet more than 10 active sweat glands measured, the size could be reduced. Alternatively, the sweat rate could be determined and the size of the one or more inlets that have an adjustable opening size could be reduced.

According to another exemplary embodiment of the present invention, the sweat sensor comprises a plurality of inlets, wherein at least some of the plurality of inlets differ in their opening size/projected cross-sectional area onto the skin. The sensor is configured for selecting inlets with a particular size, which the sensor uses for uptaking and analyzing the uptaken sweat.

It should be noted that the configuration of the sensor to select inlets with a particular size shall mean that only the sweat that is uptaken by such selected inlets will be used for processing in the next analytical cycles such that the analyzing units that analyse the sweat uptaken by such selected inlets are activated. In case all analyzing units are for example as a standard procedure activated, the processor of the sensor only processes and takes into account data that is coming from the analyzing units of such selected inlets.

An exemplary embodiment of such a selection of inlets with a particular size will be described in more detail hereinafter, for example in the context of the embodiments shown in FIGS. 1, 2 and 5.

According to another exemplary embodiment of the present invention, the sweat sensor comprises a processor, which is configured for comparing the determined sweat parameter of the user with a reference setting for the sweat parameter. The processor is configured for determining, preferably based on a result of the comparison, a target size/area of the inlet opening. The sensor is configured for considering only sweat uptaken by inlets that have an opening size with the determined target size/area.

As will be understood by the skilled reader, the processor may also be configured for determining a range of target sizes and may consider only sweat uptaken by inlets which fall within this range of target sizes/area.

As has been described hereinbefore with non-limiting examples, thresholds or reference settings may be stored within the sensor and which the sweat sensor can use to compare the currently measured values of the determined sweat parameter and may adapt the size of the openings of the one or more inlets that are used for uptaking and analyzing the uptaken sweat in the next analytical cycle accordingly.

The inventors of the present invention have found that the accuracy of a sweat sensor may be improved, if the size of the openings of the inlets, which the sensor uses for uptaking sweat which is afterwards analysed, is controlled depending on the currently measured value of the sweat parameter, like for example the sweat rate or the number of active sweat glands. In particular, the inventors found out that prior art sweat sensors can be improved in accuracy if the sweat sensor ensures that a minimum number of active sweat glands per inlet, but also, and even more important, that not too many active sweat glands per inlet are present for a sweat measurement. This embodiment is one way of ensuring that the sweat parameter is correctly measured with the appropriately sized inlets of the sensor.

According to another exemplary embodiment of the present invention, the sweat sensor has at least one inlet with an opening that is adjustable in its cross-sectional area by the sensor.

As is clear to the skilled reader, there is at least one inlet with an opening that is adjustable in its cross-sectional area projected onto the skin surface. In a preferred embodiment, the sweat sensor has at least one inlet with an opening that is adjustable in its diameter that can be controlled by the sensor.

Variable sizes of inlet openings can be achieved by for example using the same technique as for diaphragms, for example well-known mechanical diaphragms like those described in the context of the embodiment of FIG. 4. Another alternative is a more recent technology, using for example a donut-like soft hyperelastic composite hydrogel based aperture which is sensitive to heating or cooling, as described in Seo Gyun Kim et al. "Human-Iris-Like Aperture and Sphincter Muscle Comprising Hyperelastic composite Hydrogels Containing Graphene Oxide", Macromol. Mater. Eng. 2019, 304, 1800560.

The diaphragms of FIG. 4 always give a very smooth circular hole. However, also in alternative applications as shown in the embodiment of FIG. 3, a much simpler form is allowed, such as squared elements that can be mechanically and/or electrically activated to provide a larger or smaller inlet opening depending on the value of the determined sweat parameter and thresholds or reference settings that are stored in the sensor.

Of course, other materials and mechanisms can be used to provide for an inlet with an opening that is adjustable in its cross-sectional area/diameter by the sensor.

According to another exemplary embodiment of the present invention, the sweat sensor comprises a processor, which is configured for comparing the determined sweat parameter of the user with a reference setting for the sweat parameter. The processor is configured for determining a target size/area of the inlet opening. Moreover, the sensor is configured for adjusting the cross-sectional area of the at least one inlet with the adjustable opening diameter based on, or to the determined target size/area.

The sweat parameter determined by one or more analyzing units of the sensor is preferably the sweat rate of the user or the number of active glands per inlet. Based on the currently measured and thus determined value of this sweat parameter, the processor compares this with a reference setting and determines what kind of size of the inlet opening to be used for the next analytical cycle is appropriate. The sensor is thus configured for controlling the cross-sectional area (e.g. diameter) of the at least one inlet with the adjustable opening cross-sectional area/diameter to the determined target size. It may be the case, that the target size/area is defined as a range of a target size/area and the sensor may control the adjustment of the cross-sectional area/diameter of one or more size adjustable openings accordingly.

According to another exemplary embodiment of the present invention, the determined sweat parameter of the user, determined by the one or more analyzing units, is at least one of a sweat rate of the user, and a number of active sweat glands per inlet and/or per area.

The measurement and determination of the sweat rate of the user can be applied in various different manners. For example, the sweat rate can be determined with state of the art flow sensors, for example based on temperature difference. More details about such a determination of the sweat rate of the user will be provided hereinafter in more detail. However, the sweat rate can also be determined by counting a number of droplets that have a specific size. This is the method that is used for example in the sweat sensor from Eccrine Systems/University of Cincinnati, called "Digital Volume Dispensing Systems" as is proposed and described in patent application WO 2019/183529 A1.

Moreover, the determination of the sweat rate may use a measurement of the osmolality. In principle, the body of the user does not want to get rid of all ions and therefore tries to reabsorb in the sweat duct while the sweat is transported from the sweat gland, via the sweat duct, to the skin surface. However, if the sweat rate is high, this re-absorption cannot fully take place. The ions will only to a lesser extent get reabsorbed. Therefore, the concentration of certain ions, in particular $Na^+$ and $Cl^-$, in the sweat are high for high sweat rates and low for lower sweat rates. This concentration, i.e. osmolality, can thus be measured as surrogate for the sweat rate measurement. In that sense it is a proxy measurement of the sweat and can be used in an exemplary embodiment example of the present invention.

Similarly, pH can be used. Another surrogate, proxy measurement for sweat rate is the galvanic skin response (GSR), as mentioned hereinbefore and hereinafter. Therefore, the determination of the sweat rate of the user may be a direct sweat rate measurement, for example by using flow sensors, as described before and hereinafter. Alternatively or in addition, also a surrogate measurement like the measurement of the concentration of certain ions, in particular $Na^+$ and $Cl^-$, can be comprised by this embodiment of the present invention. More details about the physiological background can be found in the scientific article of Z. Sonner et al. "The microfluidics of the eccrine sweat gland, including biomarker partitioning, transport, and biosensing implications" published in Biomicrofluidics 9, 031301.

According to an exemplary embodiment of the present invention, the sweat sensor comprises a processor, which is configured for comparing a first value of the sweat parameter determined in a first analytical cycle of the sensor with a second value of the sweat parameter determined in a second analytical cycle of the sensor, the second analytical cycle being subsequent to the first analytical cycle. Moreover, the sensor is configured for decreasing the size/cross-sectional area of the opening of the one or more inlets, which the sensor uses for uptaking the sweat and uses for analyzing the uptaken sweat in the next analytical cycle, if the second value exceeds the first value.

In an example thereof, the sweat parameter is e.g. a sweat rate of the user and if it is determined by the sweat sensor that the sweat rate of the user has increased over a certain threshold, then the sensor decreases the size/area of the opening of the one or more inlets which the sensor uses for uptaking and analyzing, or generates a corresponding control signal to select the appropriate inlets having a fixed opening size. In other words, the sensor may either adjust one or more inlets which each have an opening that is adjustable in its respective cross-sectional area, e.g. diameter, by the sensor and/or the sensor selects inlets with a smaller size/area. The same can hold true for example for the number of active sweat glands per inlet that are determined by the analyzing unit or units as has been described hereinbefore. In this way, this sweat sensor ensures, that not too many numbers of active glands per inlet are used in the next analytical cycle of the processor. As has been described hereinbefore, this improves the measurement accuracy of the sweat sensor.

According to another exemplary embodiment of the present invention, the one or more analyzing units are configured for determining a sweat rate per gland of the user and the analyzing unit is configured for measuring a concentration of a biomolecule in the uptaken sweat of the user. The sensor is further configured for estimating a concentration of the biomolecule in blood of the user based on the determined sweat rate per gland and based on the measured concentration of the biomolecule in the uptaken sweat.

Biomolecules concentrations, like for example lactate, in sweat can be translated back to the concentrations in blood, and thus sweat monitoring gives an ideal unobtrusive way of monitoring a patient. A problem hampering this translation is the fact that the correlation between sweat concentrations and blood concentration depends on the sweat rate per gland. To determine the sweat rate per gland, the number of active sweat glands is determined. This number not only depends on the person and body location, but may also vary in time. Prior art sweat sensors measuring sweat rate per gland are only able to do this for a certain range of active sweat glands per surface area. The sweat sensor of the present invention however increases this range by using inlets of various sizes. Therefore, an improved estimation or determination of the concentration of the biomolecule in the blood of the user is presented.

According to another exemplary embodiment of the present invention, the sweat sensor comprises a plurality of inlets with a respective opening that is adjustable in size by the sensor. The sensor is configured for determining from the uptaken sweat a sweat rate of the user and/or a number of active sweat glands of the user. The sensor is also configured for steering all inlets of the plurality of inlets to the same opening size based on the determined sweat rate and/or based on the determined number of active sweat glands.

According to an exemplary embodiment of the invention, a flow sensor disposed in or around a channel, e.g. a fluid channel, of the sensor is presented, wherein the channel connects the at least one inlet with the analyzing unit. The flow sensor is configured for measuring the sweat rate of the sweat.

It should be noted that the term "sweat rate" is synonymously used herein with the term "excretion rate", and "sweat" or "uptaken sweat" should be understood as "excreted sweat".

According to a preferred embodiment one or more of the plurality of sample areas, in which the inlets are arranged, may comprise a channel connected to a cavity. The sensor may be a flow sensor disposed in the channel and may measure an excretion rate of excreted sweat at the sample area. The channel and the sample area may be arranged such that the excreted sweat at the sample area at least partially fills the cavity, flows into and along the channel and interacts with the flow sensor.

The channel may therefore effectively provide an outlet for the cavity, such that the sweat gathered in the cavity of the sweat flows out of the cavity through the channel The sensor may be disposed in the channel The channel may be centrally located at the top of the cavity, i.e. the top surface of the cavity which faces the surface of the skin. The channel may comprise a cylindrical channel attached to the main cavity and a rectangular channel attached to the cylindrical channel One or more biomolecule concentration sensors may be disposed in the channel The flow sensor may comprise an upstream temperature sensor; a downstream temperature sensor; and a pulsed heating element. The excretion rate may be measured by: calculating the difference between a temperature measured by the upstream temperature sensor and a temperature measured by the downstream temperature sensor with respect to the pulsed heating element to derive a flow velocity measurement; and by integrating the flow velocity measurement as a function of time to obtain the excretion rate. The pulsed heating element may be disposed between the upstream temperature sensor and the downstream temperature sensor. The sensor may be pre-calibrated in factory testing using different fluids.

According to another aspect of the present invention, a method of analyzing a user's sweat uptaken by a sensor from the user's skin is presented. The method comprises the steps of uptaking sweat from the user's skin through one or more inlets of the sensor and analyzing at least some of the uptaken sweat by an analyzing unit of the sensor. Moreover, the method comprises the step of controlling, based on a result of the analysis of the uptaken sweat, a size of an opening of the one or more inlets, which the sensor uses for uptaking sweat and for analyzing the uptaken sweat in a subsequent analysis cycle of the sensor. The control of the size is carried out by increasing or decreasing the size of an adjustable opening of the at least one inlet and/or by selecting one or more inlets with a larger opening or with a smaller opening for a next analysis cycle as compared to the size of the opening of the inlets that were used in the previous analysis cycle.

As was explained hereinbefore in detail, controlling the size should be understood as adjusting the cross sectional area of the opening of the one or more respective inlet.

The sensor that can be used for carrying out this method may have fixed size inlets with differing opening sizes/cross sectional areas of the opening, may have time varying and adjustable inlet sizes/areas and may also use a combination of both, as has been explained hereinbefore in detail. In other words, this control covers both embodiments described herein, namely to use fixed size inlets which are selectively chosen by the sensor for the next analytical cycle to uptake and analyse the sweat, as is for example explained in the context of the embodiments shown in FIG. 1, FIG. 2 and FIG. 5. This control however also applies to the other embodiment in which time varying inlet area sizes are used for example by using inlets with openings as shown in FIG. 3 and FIG. 4.

The inventors of the present invention have found in their studies that measurements and analysis of sweat of a user can be improved in the accuracy if the size/area of the inlets is adjusted based on sweat parameters of the user that are currently measured. In particular, with the method of the present invention it can for example be ensured that not a too low number of active sweat glands per inlet is used for a measurement and that not a too large number of active sweat glands is used for a measurement with such a sweat sensor. In other words, the method presented herein can ensure that an optimal size/area of an opening of the one or more inlets used for uptaking the sweat and afterwards analyzing the sweat is realized.

As was described hereinbefore, in a preferred embodiment, the step of controlling the size of the opening of the one or more inlets, which the sensor uses for uptaking the sweat and for analyzing the uptaken sweat, by changing a cross-sectional area of the opening of the one or more inlets, and/or by selecting inlets with a particular size, is carried out by a processor or a microcontroller of the sensor.

In the following, processing methods for fixed-sized inlet areas will be elucidated. There are various options for the processor to process the data. Here are the most distinct methods:

A. The processor uses the information only from the inlets of the most-appropriate size/area to determine the number of active sweat glands/the sweat gland density.
B. The processor uses the information from all the inlets to count the number of active sweat glands in the probed area.
C. The processor uses method A for a high number of active sweat glands and method B for a low number of active sweat glands.

Case A—only inlets of most-appropriate size/area:

Determining the most-appropriate size/area can be based on how many active sweat glands are measured per inlet of a particular size. If e.g. there are three sizes of inlets and most of the smallest inlets give 0 active sweat glands (e.g. on average 0.09 active sweat glands per inlet for the smallest inlets), most of the intermediate inlets give 1 or 2 active sweat glands per inlet (e.g. on average 1.5 active sweat glands per inlet for the intermediate inlets), and the largest inlets give 10 or more active sweat glands per inlet (which is a number that, because it's so big, can then not be trusted anymore), then the conclusion is that the intermediate inlets have the most appropriate size/area. In case A, only those inlets will then be used to determine the number of active sweat glands. As the area of the inlets of the intermediate size is known, also an active sweat gland density can be determined, if needed (i.e. density=number/area). There is still a choice to determine the biomarker concentration from the sweat coming from the intermediate size inlets only or to determine the concentration from all the sweat in the system, i.e. coming from all inlets. Another method to determine the most appropriate sized inlets for determining the number of active sweat glands is by using a measured sweat rate, as the sweat rate is correlated with the number of active sweat glands. For example, when the sweat rate is below 5 $nl/min/cm^2$, then the largest inlets are used, when the sweat rate is between 5 and 100 $nl/min/cm^2$ the intermediate inlets are used, and when the sweat rate is higher than 100 $nl/min/cm^2$, the smallest inlets are used.

Case B—all inlets

Using all inlets to determine the number of active sweat glands is feasible when the active sweat gland density is low. However, it becomes more inaccurate when the active sweat gland density increases, because then the bigger inlets will be fed by many active sweat glands. To solve this problem, there is option C.

Case C—use method A for high sweat rates and method B for low sweat rates

This case is to solve the problem mentioned under case B. Determining which method to use (A or B) can (similar to what was explained in case A) be based on sweat rate or on the number of determined active sweat glands.

Intermediate case—use several, but not all sizes of inlets

An example of an intermediate case is when the smallest inlets and the inlets of intermediate size are used to determine the number of active sweat glands, whereas the largest size inlets are not used for that purpose. (Note: the largest inlets might still be used in the determination of the biomarker concentration or might even not be used for that and thus being totally ignored.)

In the following, steering and processing methods for time-varying inlet size will be elucidated.

Instead of inlets that have a fixed size, inlets can be used that adapt their size in order to get an appropriate size for the current active sweat gland density. Similar to what was explained for case A in the previous section, the appropriate size/area can be based on the number of active sweat glands currently measured (e.g. when there are per inlet more than 10 active sweat glands measured, the size should be reduced) or the sweat rate (e.g. for <5 $nl/min/cm^2$ increase the size to a larger cross sectional area pf the inlet opening).

The size of the inlets can be steered individually (i.e. every inlet could take on its own best size, based on the number of active sweat glands or sweat rate determined for that particular inlet). However, as we expect the most straightforward application to be a wearable sensor, which is small and therefore covering only a small part of skin area (most probably of the order of 1 $cm^2$), a large variation in active sweat gland density over the area is not to be expected and thus steering all inlets to the same size would be appropriate.

It could be regularly checked, e.g. every second, minute or half an hour, if the size of the inlets is still appropriate or should be changed because the active sweat gland density has changed considerably. Instead of using a fixed time lapse for that, a trigger like increase/decrease of heart rate or galvanic skin conductance could be used.

As in each point of time, all inlets will have a size that is appropriate for the active sweat gland density, the sweat gathered from all inlets could be used for further analysis of e.g. a biomarker concentration.

In particular, the method can be used to determine the number of active sweat glands with the one or more analyzing units of the sensor and after the sensor has adapted the opening size/area of the inlets used for this based on a first analytical cycle of the sensor. Therefore, in a first analytical cycle, a sweat parameter of the user may be determined and the size of the opening of the one or more inlets is accordingly controlled before another analytical cycle then determines the sweat parameter and/or a biomolecule concentration in a second analytical cycle.

According to another exemplary embodiment of the present invention, the method comprises the step of determining a number of active sweat glands per inlet from which the sweat is uptaken by the sensor. Moreover, the determined number of active sweat glands is compared with a reference setting regarding this parameter of the number of active sweat glands. When the determined number of active sweat glands is below a predefined minimum number of active sweat glands defined in the reference settings, the method comprises the step of increasing the size of the opening of the at least one inlet and/or selecting one or more inlets with a larger opening for the next analysis cycle as compared to the size of the opening of the one or more inlets that were used in the previous analysis cycle. In other words, when it is determined in this method that a too low number of active sweat glands is present, the method ensures that in the next analytical cycle, the size of the opening of the used inlets is increased.

Moreover, when the determined number of active sweat glands per inlet is above a pre-defined maximum number of active sweat glands defined in the reference setting, the method comprises the step of decreasing the size/area of the opening of the at least one inlet and/or selecting one or more inlets with a smaller opening for the next analysis cycle as compared to the size of the opening of the one or more inlets that were used in the previous analysis cycle.

In other words, in case it is detected with the method that a number of active sweat glands is currently measured which is above a pre-defined maximum threshold, then the size of the opening of the used inlets is decreased.

According to another exemplary embodiment of the present invention, the method comprises the step of determining a sweat rate of the user and using the determined sweat rate for determining the number of active sweat glands per inlet from which the sweat is uptaken by the sensor.

In other words, in this embodiment it is taught to the skilled reader that the size/area of the inlets should be large when the number of active sweat glands is low and small when the number of active sweat glands is high. Moreover, the size/area of the inlets is small when the sweat rate is high and the size/area is large when the sweat rate is low. Moreover, the sweat rate can be used to get a rough estimation of the number of active sweat glands. This could also be understood as targeting a certain, in particular maximum, number of active sweat glands per inlet.

According to another aspect of the present invention, a program element for analyzing a user's sweat uptaken by a sensor from the user's skin, is presented. The program element, when being executed by a processor, is adapted to carry out analyzing at least some of the uptaken sweat by an analyzing unit of the sensor, controlling, based on a result of the analysis of the uptaken sweat, a size of an opening of one or more inlets of the sweat sensor, which the sensor uses for uptaking sweat and for analyzing the uptaken sweat in a subsequent analysis cycle, and wherein the control of the size is carried out by increasing or decreasing the size of an adjustable opening of the at least one inlet and/or by selecting one or more inlets with a larger opening or with a smaller opening for a next analysis cycle as compared to the size of the opening of the inlets that were used in the previous analysis cycle.

The program element may be part of a computer program, but it can also be an entire program by itself. For example, the program element may be used to update an already existing computer program to get to the present invention.

The program element may be stored on a computer readable medium, like a storage medium, such as for example, a USB stick, a CD, a DVD, a data storage device, a hard disk, or any other medium on which a program element as described above can be stored.

In the following different embodiments of the sweat sensor and associated methods of the present invention are described, to which was referred to hereinbefore and will be referred to hereinafter as "discretization sensor/methods". It should be understood that the corresponding sensor is configured to carry out such a method. These discretization methods are examples of a method and a sensor for determining the number of active glands per inlet or area and/or for determining the sweat rate or the sweat rate per gland, as described herein. As is clear to the skilled reader, also other methods/sensors can be used determining these parameters. These sensors and methods can be combined with the concept of the present invention to provide sweat sensor with various sized inlets and/or size adjustable inlets and methods for selection and/or adjustment thereof.

The first discretization method classifies different inlets/sample areas the sensor in uptaking discrete volume levels of sweat x, 2x, 3x, 4x etc. of sweat volume, where x is the assumed volume of sweat excreted by a single gland, i.e. the base excretion rate. The sample areas are to be understood as the areas which uptake the sweat from the skin and which are defined by the inlets.

When using this discretization method, the sweat sensor of this embodiment is configured for determining a sweat excretion rate per sweat gland of a user, and the sensor comprises a fluidic structure configured to be in contact with the skin of the user to collect sweat excreted at the surface of the skin of the user from sweat glands, the fluidic structure comprising a plurality of sample areas, each sample area comprising a cavity configured to gather excreted sweat, and two or more of the plurality of sample areas comprising an analyzing unit configured to acquire sensor data relating to an excretion rate of the excreted sweat at the sample area. Also a processor is provided which is configured to receive the sensor data from two or more of the sensors of the fluidic structure, to determine, from the received sensor data, the number of sweat glands at each sample area and a total sweat excretion rate of the sample areas; to determine a total number of sweat glands from the number of sweat glands at each sample area; and to determine a sweat excretion rate per sweat gland using the total sweat excretion rate and the total number of sweat glands.

According to an embodiment, the number of sweat glands at each sample area is determined by determining, from the received sensor data, a zero excretion rate that corresponds to zero sweat glands at a sample area such that sensor data below a predetermined threshold is categorized as zero excretion rate, determining, from the received sensor data, a base excretion rate that corresponds to one sweat gland at a sample area such that multiples of the base excretion rate correspond to multiples of one sweat gland; and categorizing the sensor data from each sample area according to the zero excretion rate, the base excretion rate and multiples of the base excretion rate to determine the number of glands at each sample area.

According to an embodiment, the processor is configured to determine the total sweat excretion rate of the sample areas by summing the sensor data from all sample areas other than sample areas categorized as zero excretion rate; determine the total number of sweat glands by summing the determined number of glands at each sample area; and determine the sweat excretion rate per sweat gland by dividing the total sweat excretion rate by the total number of sweat glands.

According to an embodiment, one or more of the plurality of cavities is segregated into a plurality of conical structures; and the center of each conical structure is in contact with the skin when the skin is in a first position and is not in contact with the skin when the skin is in a second position such that excreted sweat flows between the conical structures.

According to an embodiment, the sweat sensor comprises a concentration sensor configured to determine a concentration of a compound in the excreted sweat.

According to an embodiment, the sweat sensor comprises three or more triangularly arranged sample areas, wherein the processor is configured to determine, from the received sensor data, the excretion rate at each of the three sample areas at a first time point; determine, from the received sensor data, the excretion rate at each of the three sample areas at a second time point occurring after the first time point; calculate a first time point ratio indicating a ratio of the excretion rates at the three sample areas at the first time point; calculate a second time point ratio indicating a ratio of the excretion rates at the three sample areas at the second time point; calculate a difference between the first time point ratio and the second time point ratio; and determine, in response to the difference between the first time point ratio and the second time point ratio exceeding a predetermined threshold, degradation of the fluidic structure.

According to an embodiment, the sweat sensor comprises a supplementary fluidic structure configured to be in contact with the skin of the user to collect sweat excreted at the surface of the skin of the user from sweat glands, the supplementary fluidic structure comprising a supplementary sample area comprising a supplementary cavity configured to gather excreted sweat; a supplementary channel connected to the supplementary cavity; and a concentration sensor disposed in the supplementary channel and configured to determine a concentration of a compound in the excreted sweat, wherein the supplementary sample area is arranged such that the excreted sweat at the supplementary sample area at least partially fills the supplementary cavity, flows into and along the supplementary channel and interacts with the concentration sensor; and the size of the supplementary cavity of the supplementary fluidic structure is at least one hundred times larger than a cavity of the plurality of cavities of the fluidic structure.

According to an embodiment, the one or more of the plurality of sample areas further comprises a channel connected to the cavity; the sensor is a flow sensor disposed in the channel and configured to measure an excretion rate of excreted sweat at the sample area; and the channel and the sample area are arranged such that the excreted sweat at the sample area at least partially fills the cavity, flows into and along the channel and interacts with the flow sensor.

According to an embodiment, the flow sensor comprises an upstream temperature sensor; a downstream temperature sensor; and a pulsed heating element, wherein the excretion rate is measured by: calculating the difference between a temperature measured by the upstream temperature sensor and a temperature measured by the downstream temperature sensor with respect to the pulsed heating element to derive a flow velocity measurement; and integrating the flow velocity measurement as a function of time to obtain the excretion rate.

According to an embodiment, the sweat sensor the fluidic structure comprises a primary intersection and an exit channel connected to the primary intersection and configured to remove the excreted sweat from the fluidic structure; and one or more of the plurality of channels are connected to the primary intersection such that the excreted sweat flows through the channel, into the primary intersection and then into the exit channel According to an embodiment, the sweat sensor comprises a fluid leveler disposed in one or more of the plurality of cavities and composed of a hydrophilic material, wherein the fluid leveler is configured to direct the excreted sweat to the channel.

According to an embodiment, the sweat sensor comprises a de-bubbler configured to eliminate air bubbles formed in the excreted sweat, the de-bubbler comprising a first part comprising a plurality of hydrophilic projections arranged sequentially to define a plurality of channels between the hydrophilic projections; and a second part comprising a hydrophobic material and a vent hole, wherein the first part is disposed opposite the second part; and the de-bubbler is disposed in one or more of: a channel, and the exit channel.

According to an embodiment, the sweat sensor comprises wherein the sample areas of the plurality are arranged adjacent to each other such that excreted sweat collected in a first cavity is able to overflow into an adjacent cavity; the sensor is a coloration sensor disposed in a cavity of the plurality and configured to activate a color change of the sample area in response to interaction with excreted sweat; the sensor data is data indicating a coloration of a sample area; and the processor is configured to determine the number of sweat glands by determining, from the received sensor data, a zero excretion rate that corresponds to zero sweat glands at a sample area at which there is no coloration; determining, from the received sensor data, a base excretion rate that corresponds to one sweat gland at a sample area at which there is coloration at a single sample area; determining, from the received sensor data, multiples of the base excretion rate that corresponds to multiples of one sweat gland at a sample area at which there is coloration at multiple adjacent sample areas; and categorizing the sensor data from each sample area according to the zero excretion rate, the base excretion rate and multiples of the base excretion rate to determine the number of glands at each sample area.

According to an embodiment, the processor is configured to determine the sweat excretion rate at each sample area other than sample areas categorized as zero excretion rate by dividing the volume of the cavity by the time taken for the colorization to occur at the sample area; determine the total sweat excretion rate of the sample areas by summing the determined sweat excretion rate at all sample areas other than sample areas categorized as zero excretion rate; determine the total number of sweat glands by summing the determined number of glands at each sample area; and determine the sweat excretion rate per sweat gland by dividing the total sweat excretion rate by the total number of sweat glands.

The aforementioned sensor embodiments relate to the first discretization method, which is described now as method embodiments.

According to an embodiment a method for determining a sweat excretion rate per sweat gland of a user is presented, the method comprises collecting, by a fluidic structure, sweat excreted at the surface of the skin of the user from sweat glands, by gathering excreted sweat at a plurality of sample areas of the fluidic structure in a cavity, each sample area comprising a cavity; acquiring, as sensor data from two or more sensors at one or more of the plurality of sample areas, an excretion rate of the excreted sweat measured at the sample area; receiving, by a processor, the sensor data from two or more of the sensors of the fluidic structure; determining from the received sensor data, the number of sweat glands at each sample area and a total sweat excretion rate of the sample areas; determining a total number of sweat glands from the number of sweat glands at each sample area; and determining a sweat excretion rate per sweat gland using the total sweat excretion rate and the total number of sweat glands.

In a preferred embodiment, the sensor data is an excretion rate/sweat rate measured at the inlet/sample area; and the number of sweat glands at each sample area is determined by determining, from the received sensor data, a zero excretion rate that corresponds to zero sweat glands at a sample area such that sensor data below a predetermined threshold is categorized as zero excretion rate; determining, from the received sensor data, a base excretion rate that corresponds to one sweat gland at a sample area such that multiples of the base excretion rate correspond to multiples of one sweat gland; and categorizing the sensor data from each sample area according to the zero excretion rate, the base excretion rate and multiples of the base excretion rate to determine the number of glands at each sample area.

This first discretization method and the correspondingly configured sensor embodiment of the present invention has been used, for example, in the embodiment shown in FIG. 10.

In the following the second discretization method and the corresponding sensor configuration is described. The essence of the second discretization method is that inside the sensor, the number of active sweat glands can be determined, as described hereinafter. It makes use of the fact that each eccrine sweat gland produces its sweat in bursts; a relatively short period in which sweat is produced, followed by a longer period in which no sweat is produced (e.g. 30 seconds of sweat production and 90 seconds no sweat production).

Thus, according to an embodiment of the present invention, the sweat sensor, in particular the one or more analyzing units, are configured for sensing sweat droplets. Furthermore, the sweat sensor is configured for receiving sweat from one or more sweat glands and transporting the sweat as discrete sweat droplets to the one or more analyzing units. Furthermore, a processor is comprised, which is configured for recording the sweat droplets sensed by the one or more analyzing unit during a time period. The processor is further configured for determining time intervals between consecutive sensed sweat droplets during the time period; and is configured for identifying, using the time intervals, at least one active period of each of the one or more sweat glands during which the respective sweat gland is excreting sweat, and at least one rest period of each of the one or more sweat glands during which the respective sweat gland is not excreting sweat, the active and rest periods being assigned to the one or more sweat glands.

In a preferred embodiment the processor is further configured for determining the number of sweat glands to which the active and rest periods are assigned.

In another embodiment, the processor is further configured to receive a measure of the volume of each of the recorded sweat droplets; and determine the sweat rate per gland from the number of recorded sweat droplets, the measure of the volume of each of the recorded sweat droplets, and the determined number of sweat glands; optionally wherein the processor is configured to identify the at least one active period and the at least one rest period based on the measure of the volume of each of the recorded sweat droplets and the time intervals.

In another embodiment, the one or more analyzing unit/sensor is configured to sense an indicator of the volume of the sweat droplets, and the processor is configured to receive the sensed indicator.

In another embodiment, the processor is configured to fit data received from the sensor to a first template model, thereby to identify the active and rest periods of each of the one or more sweat glands, the data comprising at least the time intervals, and the measure of the volume of each of the recorded sweat droplets.

In another embodiment, the fitting to the first template model additionally uses: a number of sweat droplets in the at least one active period, a duration of the at least one active period, and/or a duration of the at least one rest period.

In another embodiment, wherein the processor is configured to assess a goodness of fit of the data to the first template model, and optionally, based on the goodness of fit, fit at least a portion of the data to a further first template model.

In another embodiment, the processor is configured to, following fitting the data to the first template model, fit at least a portion of the data to a second template model, wherein the first template model is based on at least some of the sweat droplets deriving from a sweat sample constituted by sweat excreted from a single sweat gland, and the second template model is based on at least some of the sweat droplets deriving from a further sweat sample constituted by sweat excreted from two or more sweat glands.

In another embodiment, the sensor is arranged to transport sweat droplets having a predetermined volume to the one or more analyzing units.

In another embodiment, the sensor comprises a sensing device for detecting a parameter relating to the concentration of an analyte whose concentration varies as a function of sweat rate, wherein the processor is configured to use the parameter in assigning the active and rest periods to the one or more sweat glands.

In another embodiment, the sensing device is a conductivity sensor and the parameter is conductivity.

In another embodiment, the sensor comprises a biomarker sensor; optionally wherein the processor is configured to receive a plurality of biomarker concentrations from the biomarker sensor during the at least one active period of a respective sweat gland and determine a variation of the biomarker concentration in time within the at least one active period.

The aforementioned sensor embodiments relate to the second discretization method, which is described now as method embodiments.

The method comprises the steps of receiving sweat from one or more sweat glands; transporting the sweat as discrete sweat droplets to an analyzing unit; sensing the sweat droplets using the sensor during a time period; recording the sweat droplets sensed during the time period; determining time intervals between consecutive sensed sweat droplets during the time period; and identifying, using the time intervals, at least one active period of each of the one or more sweat glands during which the respective sweat gland is excreting sweat, and at least one rest period of each of the one or more sweat glands during which the respective sweat gland is not excreting sweat, the active and rest periods being assigned to the one or more sweat glands.

In another embodiment the method further comprises determining the number of sweat glands to which the active and rest periods are assigned.

In a further embodiment the method further comprises receiving a measure of the volume of each of the recorded sweat droplets, and determining the sweat rate per gland from the number of recorded sweat droplets, the measure of the volume of each of the recorded sweat droplets, and the determined number of sweat glands; optionally wherein the identifying the at least one active period and the at least one rest period is based on the measure of the volume of each of the recorded sweat droplets and the time intervals.

A particular, non-limiting example of a sensor and a method using the second discretization method is described for and shown in FIG. 11.

In the following, the second discretization method and sensor is described with a focus on the processing aspect.

According to an embodiment of the present invention, the sweat sensor, in particular the one or more analyzing units, is configured for sensing sweat droplets and for receiving sweat from one or more sweat glands and transporting the sweat as discrete sweat droplets to the sensor. It comprises a processor configured to record the sweat droplets sensed by the one or more analyzing units during a time period, determine time intervals between consecutive sensed sweat droplets during the time period; and identify, using the time intervals, at least one active period of each of the one or more sweat glands during which the respective sweat gland is excreting sweat, and at least one rest period of each of the one or more sweat glands during which the respective sweat gland is not excreting sweat, the active and rest periods being assigned to the one or more sweat glands.

According to another embodiment, the processor is further configured to determine the number of sweat glands to which the active and rest periods are assigned.

According to another embodiment, the processor is further configured to receive a measure of the volume of each of the recorded sweat droplets; and determine the sweat rate per gland from the number of recorded sweat droplets, the measure of the volume of each of the recorded sweat droplets, and the determined number of sweat glands; optionally wherein the processor is configured to identify the at least one active period and the at least one rest period based on the measure of the volume of each of the recorded sweat droplets and the time intervals.

According to another embodiment, the sensor/one or more analyzing units are configured to sense an indicator of the volume of the sweat droplets, and the processor is configured to receive the sensed indicator.

According to another embodiment, the processor is configured to fit data received from the sensor to a first template model, thereby to identify the active and rest periods of each of the one or more sweat glands, the data comprising at least the time intervals, and the measure of the volume of each of the recorded sweat droplets.

According to another embodiment, the fitting to the first template model additionally uses: a number of sweat droplets in the at least one active period, a duration of the at least one active period, and/or a duration of the at least one rest period.

According to another embodiment, the processor is configured to assess a goodness of fit of the data to the first template model, and optionally, based on the goodness of fit, fit at least a portion of the data to a further first template model.

According to another embodiment, the processor is configured to, following fitting the data to the first template model, fit at least a portion of the data to a second template model, wherein the first template model is based on at least some of the sweat droplets deriving from a sweat sample constituted by sweat excreted from a single sweat gland, and the second template model is based on at least some of the sweat droplets deriving from a further sweat sample constituted by sweat excreted from two or more sweat glands.

According to another embodiment, the sensor is arranged to transport sweat droplets having a predetermined volume to the sensor.

According to another embodiment, the one or more analyzing units comprise a sensing device for detecting a parameter relating to the concentration of an analyte whose concentration varies as a function of sweat rate, wherein the processor is configured to use the parameter in assigning the active and rest periods to the one or more sweat glands.

According to another embodiment, the sensing device is a conductivity sensor and the parameter is conductivity.

According to another embodiment, the sensor comprises a biomarker sensor; optionally wherein the processor is configured to receive a plurality of biomarker concentrations from the biomarker sensor during the at least one active period of a respective sweat gland and determine a variation of the biomarker concentration in time within the at least one active period.

The aforementioned sensor embodiments relate to the processing aspects of the second discretization method, which is described now as method embodiments.

A method is presented with the steps of receiving sweat from one or more sweat glands; transporting the sweat as discrete sweat droplets to one or more analyzing units of a sweat sensor; sensing the sweat droplets using the one or more analyzing units during a time period; recording the sweat droplets sensed during the time period; determining time intervals between consecutive sensed sweat droplets during the time period; and identifying, using the time intervals, at least one active period of each of the one or more sweat glands during which the respective sweat gland is excreting sweat, and at least one rest period of each of the one or more sweat glands during which the respective sweat gland is not excreting sweat, the active and rest periods being assigned to the one or more sweat glands.

According to an embodiment, determining the number of sweat glands to which the active and rest periods are assigned, is comprised.

According to an embodiment, the method comprises receiving a measure of the volume of each of the recorded sweat droplets; and determining the sweat rate per gland from the number of recorded sweat droplets, the measure of the volume of each of the recorded sweat droplets, and the determined number of sweat glands; optionally wherein the identifying the at least one active period and the at least one rest period is based on the measure of the volume of each of the recorded sweat droplets and the time intervals.

As has been explained hereinbefore in detail, the methods and sensor that use the first and/or the second discretization method can be used together with the sensor and method of the present invention. Thus, the methods and sensor of the discretization methods are disclosed as embodiments of the present invention. This will be emphasized by the embodiments of FIGS. 10 and 11.

These and other features of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
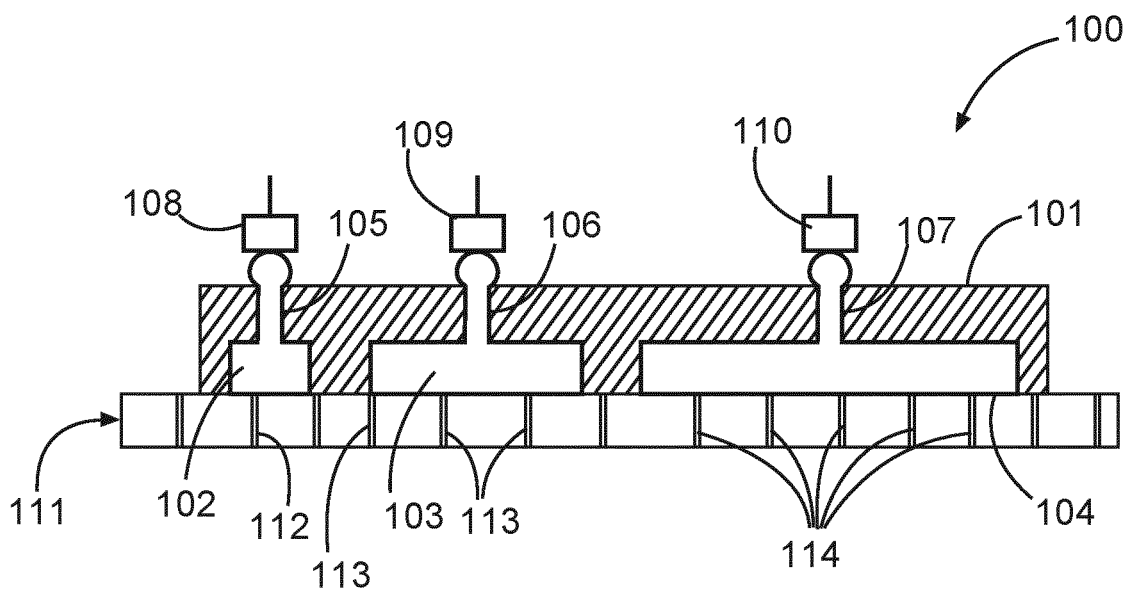
FIG. 1 schematically shows a sweat sensor for analyzing a user's sweat uptaken from a user's skin into the sweat sensor according to an exemplary embodiment of the present invention.

FIG. 1 shows a sweat sensor 100 for analyzing a user's sweat that is uptaken from a user's skin 111 into the sweat sensor 100. The sensor 100 comprises three inlets 102, 103 and 104 through which the user's sweat can be uptaken into the sensor 100. Each inlet 102, 103 and 104 is connected via respective fluid channels 105, 106 and 107 with an analyzing unit 108, 109 and 110. In this way, the sweat uptaken by the inlet with the smallest opening 102 is analyzed by analyzing unit 108 independently from the other sweat uptaken by the remaining inlets 103 and 104. The same holds true of course for inlets 103 and 104 and their independent analyzing units 109 and 110. The sweat sensor 100 may of course comprise additional components like a processor to further process the analyzed data, which is for the ease of illustration however not shown. Within the housing 101, there are thus three different sample areas provided by means of the differently sized inlets 102, 103 and 104. The analyzing units 108, 109 and 110 may be configured for determining, based on the respectively uptaken sweat, for example the sweat rate of the user and/or the number of active sweat glands per inlet, as has been described hereinbefore and will be described hereinafter. Moreover, the sweat sensor 100 is configured for controlling, i.e. selecting, a size of the opening of the inlets, which the sensor uses for uptaking the sweat and for analyzing the uptaken sweat. For example, the sensor 100 determines in a first analytical cycle by analyzing the uptaken sweat of each inlet 102, 103 and 104 the number of active glands per inlet. This determination is carried out by analyzing units 108, 109 and 110. As can be seen from FIG. 1, the inlet with the smallest sized opening 102 receives sweat from only one gland 112 of the user's skin 111. The medium sized inlet 103 receives sweat from three glands 113 and the large sized inlet 104 receives sweat from five sweat glands 114 of the user's skin. A processor of the sweat sensor 100, which is not shown here, is configured for comparing the determined number of glands per inlet with a reference setting that has been previously defined. Such a predefined reference setting may be stored within a storage medium internally or externally of the sensor. This reference setting may for example define that only inlets shall be used, in the sense of that the sweat uptaken by such inlets is analyzed and the data of this analysis will be further processed by the sensor, if at least two active sweat glands are extracting sweat into the inlet and at most four active sweat glands are extracting sweat into the inlet. The processor of the sweat sensor 100 therefore determines that only inlet 103 shall be used for the next analytical cycle of the sensor such that the further measurements and analysis of the sensor is in the future only be carried out with inlet 103 and analyzing unit 109. In this way, the sensor controls the size, i.e. selects the size of the inlets to be actively used. This may improve the accuracy of measurements done by the sweat sensor, for example the determination of the number of active sweat glands in subsequent analytical cycles, and hence also the determination of a biomolecule concentration in sweat and blood of the user can be improved.

In other words, the sweat sensor 100 shown in FIG. 1 ignores the sweat that is uptaken in future analytical cycles by the inlets 102 and 104. In another exemplary embodiment based on the one shown in FIG. 1, the sensor could be configured for determining with the analyzing units 108, 109 and 110 the sweat rate and a corresponding reference setting could be stored with respect to a desired target size of the inlet opening which is dependent on the determined sweat rate.

Moreover, after the sensor controls the size to the appropriate inlet size as described before, the analyzing units 108, 109 and 110 measure the sweat rate with the correctly sized inlet openings, determine the number of glands and determine the sweat rate per gland. For example, one or more of the discretization methods described hereinbefore can be used for such measurements/determinations. The analyzing units 108, 109 and 110 also measure/determine the concentration of a biomolecule in the uptaken sweat of the user. The sensor 100 is configured for estimating a concentration of the biomolecule, e.g. lactate, in blood of the user based on the determined sweat rate per gland and based on the measured concentration of the biomolecule in the uptaken sweat. Due to the appropriate size setting for the opening of the inlets used by the sensor, the overall measurement results of the sensor, in particular the final estimation of the concentration of the biomolecule in the user's blood, are more accurate as compared to the prior art.

Figure 2:
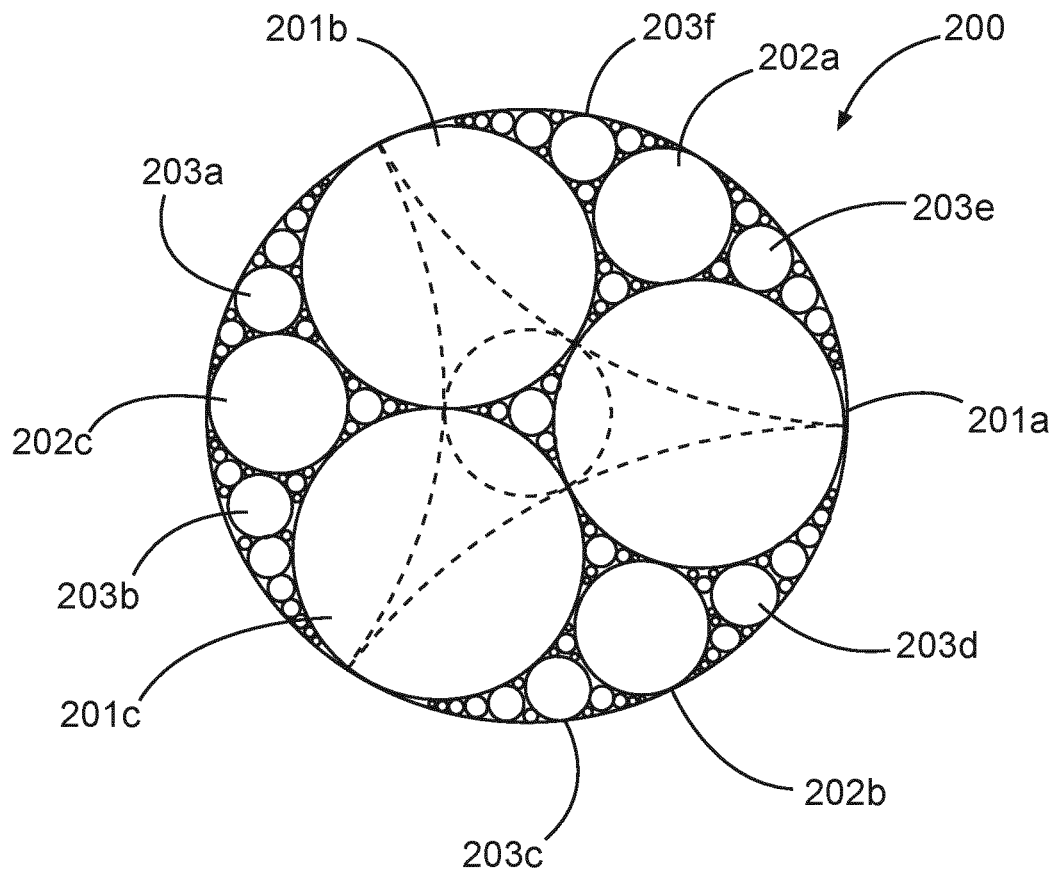
FIG. 2 schematically shows a sweat sensor with a plurality of differently sized inlet openings according to an exemplary embodiment of the present invention.

FIG. 2 schematically shows a bottom view of a sweat sensor 200 according to an exemplary embodiment of the present invention. In this bottom view it can be seen that the sensor 200 has a plurality of inlets which differ in their opening size. The sensor 200 is configured for selecting inlets with a particular size, which the sensor uses for uptaking and analyzing the uptaken sweat for the next analytical cycle of the sensor. The selection of the inlets with such a particular size can be based on a determined sweat parameter of the user and can be based on a comparison with a reference setting or a threshold, as has been described hereinbefore and will be described hereinafter. Sensor 200 comprises a first group of inlets 201a, 201b and 201c that have the same size and that have the largest size of the openings shown in FIG. 2. Moreover, sensor 200 comprises three inlets with openings 202a, 202b and 202c with a slightly smaller opening diameter of the inlet. Furthermore, there is a third group of a plurality of inlets which have the same size, which are shown with reference signs 203a to 203f. This non-limiting example of a combination of openings of the sweat sensor 200 is just one possible configuration of inlets of multiple sizes packed together.

As sweat is usually led from the skin up into the sensor via cylindrical shaped channels, the inlets are generally circular as shown in FIG. 2. Nevertheless, the present invention does not exclude other shapes like for example squared openings. As can be gathered from FIG. 2, there is only little void space between the inlets which is desired in order to keep the sensor small, making it less obtrusive for the wearer. The sensor 200 can of course be configured for selecting the inlets having a particular size based on a sweat parameter that has been determined from the sweat uptaken by the user and based on a comparison the sensor does with for example a reference setting. A corresponding control signal for activating for example only the analyzing units associated with openings 201a to 201c is one non-limiting option.

Figure 3A:
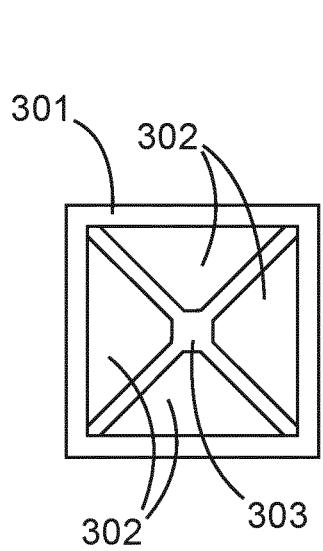
FIG. 3 schematically shows an inlet with an opening that is adjustable in its diameter by a sweat sensor according to an exemplary embodiment of the present invention.
Figure 3B:
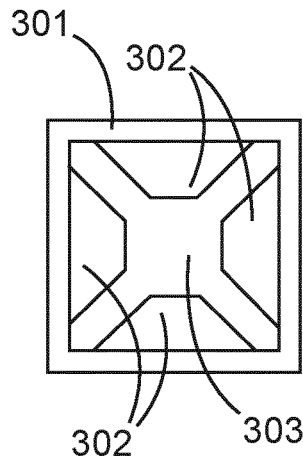
Figure 3C:
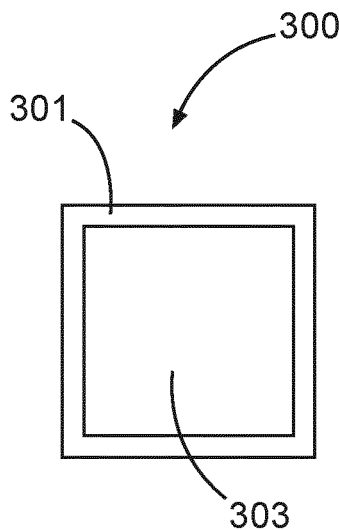

FIG. 3 schematically shows an inlet 300 with an opening 303 that is adjustable in its cross-sectional area projected onto the skin by a sensor according to an exemplary embodiment of the present invention. As can be seen from FIG. 3A on the left-hand side, the inlet 300 comprises a frame 301 in which four movable mechanical elements 302 are positioned. In FIG. 3A, the four movable mechanical elements 302 are in such a position, that they define the smallest possible inlet opening 303. In FIG. 3B, however, the mechanical elements 302 are adjusted slightly different by the corresponding sensor such that the opening 303 provided by the inlet 300 is medium sized. In FIG. 3C, the sensor 300 has adjusted the mechanical elements 302 such that the opening of the inlet 300 has a maximal size. The adjustment of the mechanical elements 302 can be based on a control signal issued by a microcontroller or a processor of the sweat sensor. The sweat sensor can generate such a control signal based on for example the sweat rate of the user that has been measured in a previous analytical cycle or based on the number of active sweat glands that was determined for this inlet 300 in a previous analytical cycle.

To make sure that only the sweat is captured from the open inlet and not from underneath the material surrounding it (i.e. the part that opens or closes in order to vary the size), this material could be covered by a sponge or wick that gets in contact with the skin to absorb the sweat in that area.

Figure 4:
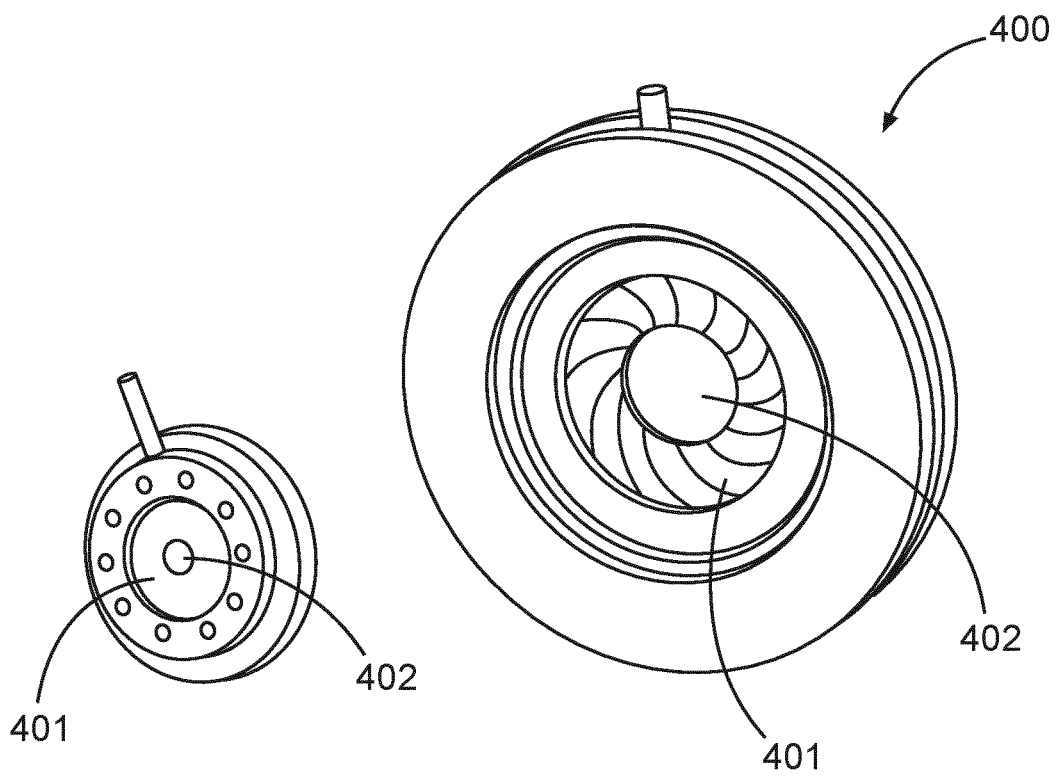
FIG. 4 schematically shows a diaphragm mechanism used as an inlet with an opening that is adjustable in its diameter by a sensor according to an exemplary embodiment of the present invention.

FIG. 4 schematically shows another embodiment of an inlet with an opening that is adjustable in its diameter by a sensor according to an exemplary embodiment of the present invention. FIG. 4 schematically shows a diaphragm mechanism 400 that uses a plurality of movable lamella 401 to define and adjust the diameter of the opening 402. Such a mechanical mechanism may also be used not only in one inlet of the sensor but also for a plurality of inlets. In an alternative or in combination also hyperelastic composite hydrogels may be used which react on heating and cooling in order to adapt the diameter of the opening. Such an inlet 400 can thus be implemented in a sweat sensor according to an exemplary embodiment of the present invention to control the size of the opening.

Figure 5:
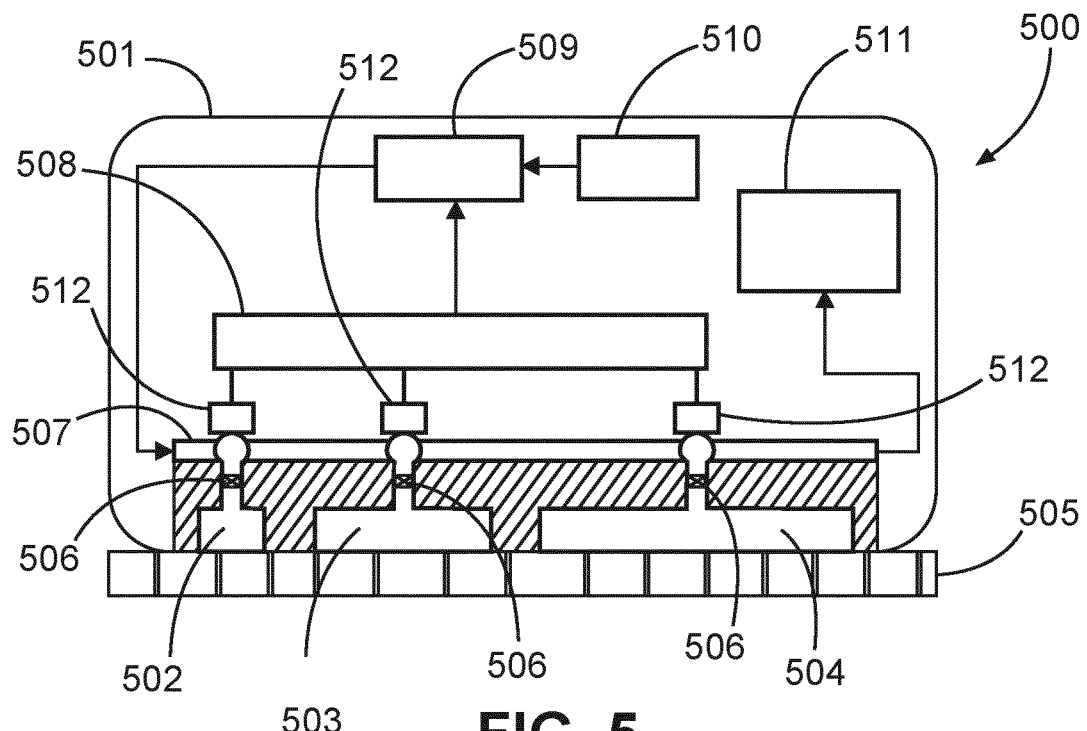
FIG. 5 schematically shows a sweat sensor with an adaptive selection of the inlet size/area according to an exemplary embodiment of the present invention.

FIG. 5 schematically shows another sweat sensor 500 according to an exemplary embodiment of the present invention. The sensor 500 comprises a housing 501 in which three differently sized inlets 502, 503 and 504 are located. In each fluid/liquid channel connecting the inlet with the respective analyzing units 512 carrying out a fluid flow rate/pressure measurement, at least one valve 506 for closing an opening the fluid channel is comprised. In this embodiment of FIG. 5, the sensor 500 comprises a separate analyzing unit 511 for analyzing the sweat, where e.g. biomolecules can be measured in the sweat. In a particular embodiment, the analyzing unit 511 is configured for measuring a concentration of a biomolecule in the uptaken sweat of the user, and the sensor is configured for estimating a concentration of the biomolecule in blood of the user based on the determined sweat rate per gland and on the measured concentration of the biomolecule in the uptaken sweat.

In FIG. 5 the sweat sensor 500 comprises an array of valves 506 and a microfluidic system 507 to transport the sweat of the skin 505 from each inlet to the associated analyzing unit 512. In the embodiment of FIG. 5, a sweat rate controlled selection of the inlets with appropriate size/cross sectional area is presented, as will be explained in detail now. The fluid flow (rate)/pressure measurement analyzing units 512 can be embodied as sweat detectors which are based on a fluid flow sensor, or a GSR sensor or for example as an electrochemical sensor. The reference settings that are stored in element 510 may thus be a reference value for e.g. the fluid flow, for the sweat rate or for the osmolality. The sweat rate signals per inlet are collected in element 508 and are transferred via an electrical connection to the microcontroller 509. As is understood by the skilled reader, the microcontroller comprises a processor as was described hereinbefore. The microcontroller 509 can read out the reference settings that are stored in element 510. Based on the received sweat rate signals per inlet and the reference settings, the microcontroller can send an electrical signal to the microfluidic system 507 such that the inlets with the most suitable size is used for the next analytical cycle of the sensor 500, i.e., closes all valves 506 which are not suitable. After this adaptive selection of the most suitable inlets, the sweat sensor 500 may transfer the sweat uptaken in the next analytical cycle via the microfluidic system 507 to the actual sweat analyzing unit 511 of sensor 500 which measures now with the correctly selected inlets a desired parameter, like e.g. the concentration of a biomolecule in the uptaken sweat. It should be noted that a method associated with the sensor 500 will be described later on in the context of FIG. 8.

Figure 6:
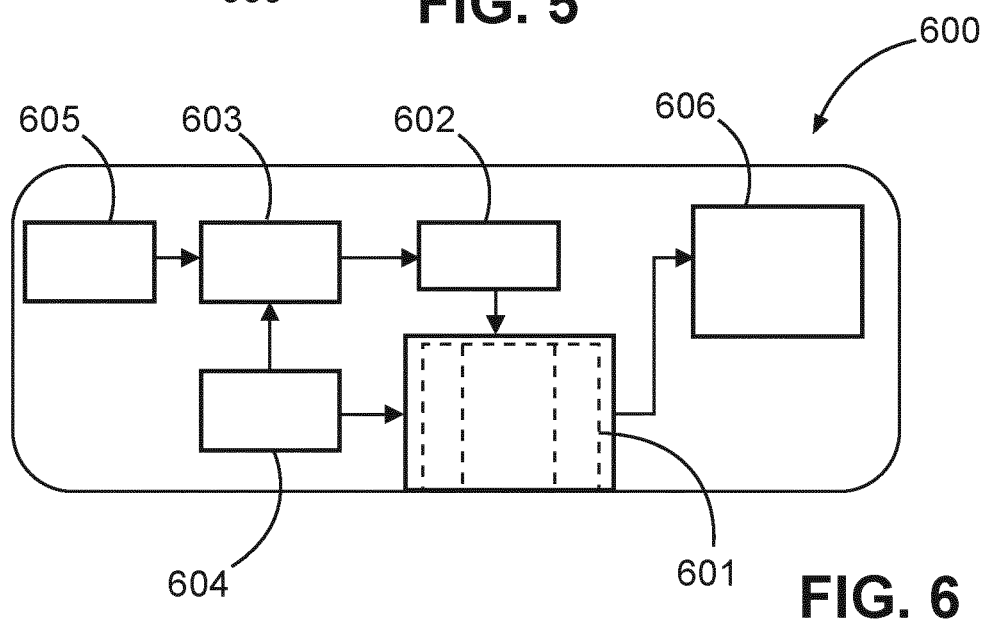
FIG. 6 schematically shows a sweat sensor with an adaptive cross-sectional area or diameter of the inlet size according to an exemplary embodiment of the present invention.

FIG. 6 schematically shows a sweat sensor 600 with an inlet that can vary in its size/area, for example by means of a diaphragm mechanism. Sensor 600 comprises an adaptive inlet geometry 601 which can be adapted in its size of opening by the mechanical actuator 602. The sweat that is uptaken in a first analytical cycle by inlet 601 is analyzed by analyzing unit 604. This analyzing unit may be for example a fluid flow sensor, a GSR sensor or an electrochemical sensor. Reference settings are stored in element 605 such that the microcontroller 603 can compare the results of the analyzing unit 604 with the reference settings. Also this microcontroller 603 may comprise a processor for its purposes described herein. The analyzing unit 604 has determined a desired parameter of the sweat such as for example the sweat rate. The reference setting may then define what kind of opening area, i.e. cross-sectional area like e.g. diameter of the adjustable inlet is preferred for the currently measured sweat rate. A corresponding electronic signal can be sent to the mechanical actuator by the microcontroller 603. The cross-sectional area or diameter of the adaptive inlet 601 is thus accordingly adjusted. In the next analytical cycle, the sweat uptaken by the inlet 601 can then be transferred to a measurement unit 606, i.e. the actual biomarker measurement unit, which determines and measures a sweat parameter of the sweat that was then uptaken with the correctly sized inlet. It should be noted that an associated method of the sensor 600 is described in the context of FIG. 9 hereinafter.

Figure 7:
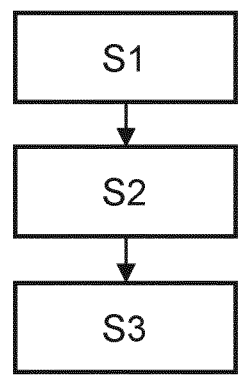
FIG. 7 schematically shows a flow diagram of a method of analyzing a user's sweat uptaken by a sensor from the user's skin according to an exemplary embodiment of the present invention.

FIG. 7 schematically shows a method of analyzing a user's sweat uptaken by a sensor from the user's skin. The method of FIG. 7 comprises the uptaking of sweat from the user's skin through one or more inlets of the sensor which is shown with step S1. Moreover, the step of analyzing at least some of the uptaken sweat with an analyzing unit of the sensor is shown with step S2. Moreover, step S3 defines the controlling, based on the result of the analysis of the uptaken sweat, the size of the opening of the one or more inlets, which the user will use for uptaking sweat and for analyzing the uptaken sweat in a subsequent analysis cycle.

If biomolecule concentrations in sweat are translated back to the concentrations in blood, such a sweat monitoring gives an ideal unobtrusive way of monitoring a patient. A problem hampering this translation is the fact that the correlation between sweat concentrations and blood concentrations depends on the sweat rate per gland. Thus, in the method described in FIG. 7, for determining the sweat rate per gland, the number of active sweat glands are more reliably determined over a larger range of active sweat glands. Prior art sweat sensors measuring the sweat rate per gland are only able to do this for a certain range of active sweat glands per inlet/surface area. The method of FIG. 7 increases this range by selectively using inlets of various sizes. In addition, methods suitable to execute either an adaptive selection or dynamic adaptation of these inlets of various sizes, i.e., dynamic range of active sweat glands per surface area, using the sweat rate (e.g. fluid flow, GSR, osmolality) as a trigger/control signal. Also the combination of adaptive selection and dynamic adaptation is of course possible in an embodiment.

Figure 8:
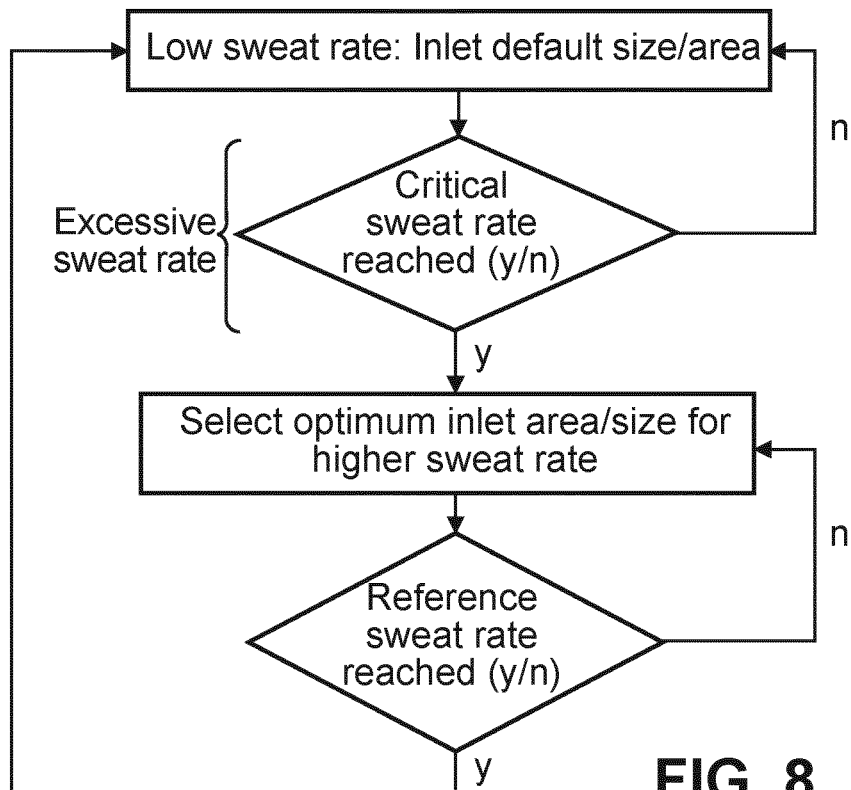
FIG. 8 schematically shows a flow-chart of a method of adaptively selecting a size of one or more openings of a sensor according to an exemplary embodiment of the present invention.

FIG. 8 schematically shows a flow diagram of a method of analyzing a user's sweat uptaken by a sensor and for controlling a corresponding sweat sensor. The method shown in FIG. 8 can for example be used to control the sweat sensor 500 shown in FIG. 5. The method shown in FIG. 8 comprises the use of a default size or area of the inlets used for uptaking and analyzing the uptaken sweat when a low sweat rate is measured. However, when a critical sweat rate is reached due to excessive sweating, then the control signal can be used to select the inlets which have an optimal inlet size or inlet area for such higher sweat rate. As it has been explained hereinbefore, the inventors of the present invention have found that sweat measurements are inaccurate if more than a certain number of active sweat glands per inlet are used and hence for an excessive sweat rate a smaller sized inlet or a plurality of smaller sized inlets should be selected for sweat measurements. If at a later point in time the sensor determines that the sweat rate has decreased and a reference sweat rate is reached (e.g. corresponding to low sweating or sweating in the sedentary state), the sensor may again be controlled such that the inlets with a default size are again used for the future analytical cycles of the sensor. This logic and control method is depicted in FIG. 8.

Figure 9:
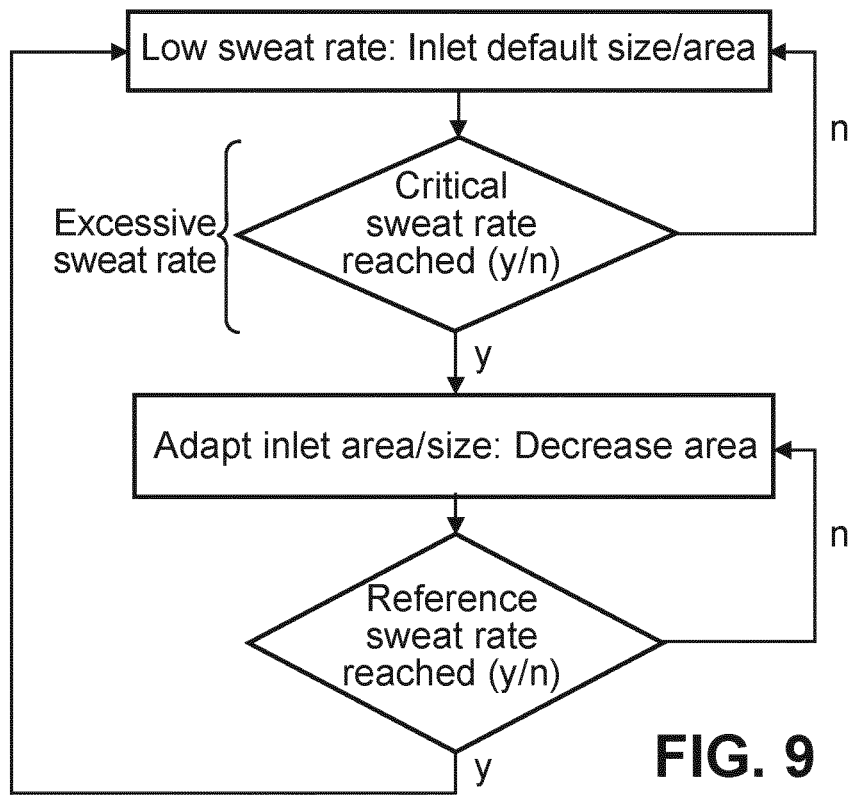
FIG. 9 schematically shows a flow-chart of a method of dynamically adapting a size of one or more inlets of a sensor according to an exemplary embodiment of the present invention.

FIG. 9 shows a flow-chart for a method of a sweat sensor with a dynamic adaption of the inlet size. In case a low sweat rate is determined by the sensor, a default inlet size is used by the sensor. If, however, it is determined that a critical sweat rate is reached, which exceeds for example a predefined threshold value, then the sensor is controlled such that it adapts the inlet size such that the size is decreased.

Figure 10:
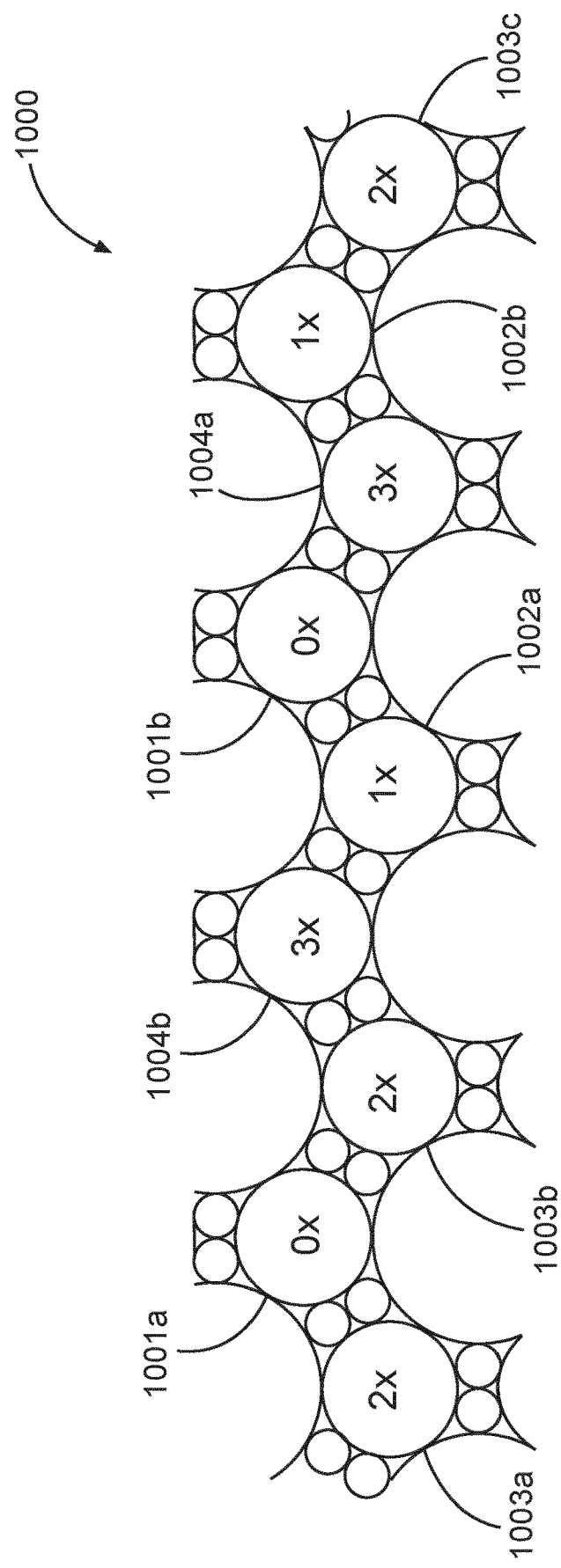
FIG. 10 schematically shows a sweat sensor according to an exemplary embodiment of the present invention, which determines the number of active glands per inlet using the first discretization method.

In the sensor embodiment of the present invention shown in FIG. 10, the first discretization method has been used. Here the present invention is used in the sense that the largest inlets and the smallest inlets are excluded, i.e. by a corresponding control signal of the sensor, and only the middle-sized inlets are taken into account for measurements of the next or for even more analytical cycles of the sensor. In other words, the sensor of FIG. 10 is configured to select the middle-sized inlets for the next analytical cycle based on the number of active sweat glands that were previously determined by the sensor from measurements in the first analytical cycle. The amounts of sweat measured from each inlet in the sweat sensor of FIG. 10 are 0, 1, 2, or 3 times x, where x is for example 2 nl/min, so the actual values measured are e.g. 4.1 nl/min, 0.01 nl/min, 3.9 nl/min, 6.2 nl/min, 1.9 nl/min, 0.02 nl/min, 5.8 nl/min, 2.0 nl/min, 4.1 nl/min, from left to right inlet. It is then determined by the sensor that the number of active glands are 2, 0, 2, 3, 1, 0, 3, 1, 2, respectively.

Figure 11:
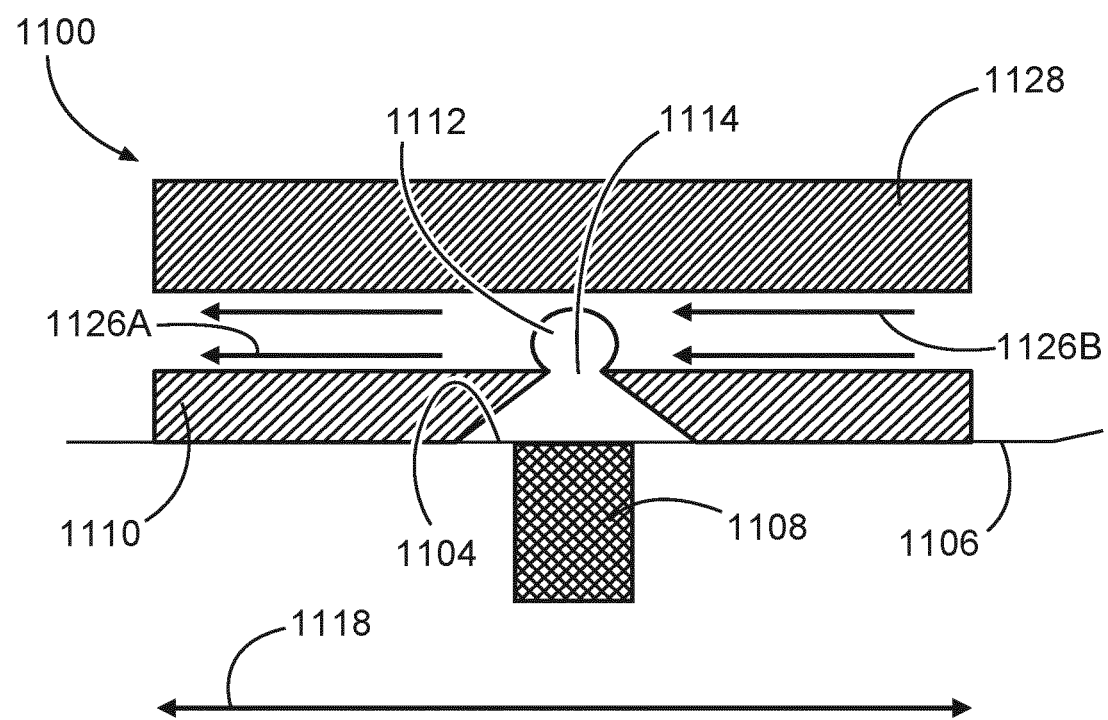
FIG. 11 schematically shows a sweat sensor according to an exemplary embodiment of the present invention, which determines the sweat rate/the swat rate per gland with the second discretization method as disclosed herein.

FIG. 11 shows a sensor 1100 according to an exemplary embodiment of the present invention, which uses the second discretization method as was described in detail hereinbefore. The inlet 1104 of the sensor 1100 is shown proximal to a sweat gland 1108. The sensor 1100 either comprises one or more inlets that are size adjustable, as shown in e.g. FIGS. 3 and 4, and the sensor adjusts that size based on the measured sweat parameter. Alternatively or in addition it comprises a plurality of inlets 1104, and at least some of the plurality of inlets differ in their opening size, and the sensor is configured for selecting inlets with a particular size, which the sensor uses for uptaking and analyzing the uptaken sweat in the next analytical cycle.

The sweat excreted by the sweat gland 1108 enters and fills the chamber via the inlet 1104. As shown in FIG. 11, the sensor 1100 may comprise a plate 1110 which is attached to the surface of the skin 1106. To compensate for the limited amounts of sweat being received into an individual chamber, the sensor 1100 may, for instance, include a plurality of such chambers, defined by such inlets 1104 for example 2 to 50 chambers, such as 10 to 40 chambers, e.g. about 25 chambers.

Once the inlet 1104 has been filled with sweat, a sweat droplet 1112 protrudes from an outlet 1114 of the chamber. In the example shown in FIG. 11, the outlet 1114 is delimited by an upper surface of the plate 1110, and a hemispherical sweat droplet 1112 forms on top of the outlet 1114 once the chamber has been filled with sweat. More generally, the sweat sensor 1100 may be configured such that the speed of formation of the sweat droplet 1112 is determined by the sweat rate, while the volume of the sweat droplet 1112 can be determined by a fluid transport assembly of the sensor.

The sensor 1100 may enable the formation of relatively uniformly sized sweat droplets 1112, and in addition may handle variable sweat droplet 1112 volumes as well. Regarding the latter, the one or more analyzing units to which the sensor 1100 transports the sweat droplets 1112 may be configured to both count the sweat droplets 1112 and determine the time it takes for each sweat droplet 1112 to pass through the analyzing unit. FIG. 11 shows an example in which sweat droplet 1112 detachment is achieved with a fluid transport assembly in which the upper surface of the plate 1110 and the lower surface of the further plate 1128 are both provided with a passive gradient, e.g. a chemical and/or topological gradient. In this respect, the arrows 1126A and 1126B respectively denote the direction of the gradient provided on the upper surface of the plate 1110 and the lower surface of the further plate 1128 for transporting the sweat droplet 1112 towards the analyzing unit.

Defined sweat droplet 1112 detachment may alternatively or additionally be achieved by a fluid transport assembly applying a pressure gradient to the sweat droplet 1112 protruding from the outlet 1114. This may be considered as an example of providing an active gradient in order to overcome the contact angle hysteresis of the sweat droplet 1112, since the fluid transport assembly actively applies a pressure/force to the sweat droplet 1112 in order to overcome the contact angle hysteresis of the sweat droplet 1112.

The pressure gradient may, for example, be applied by contacting the protruding sweat droplet 1112 with a flow of carrier fluid. The carrier fluid is preferably a fluid with which the sweat droplet 1112 is immiscible. By virtue of the sweat droplet 1112 being thus substantially prevented from mixing with the carrier fluid, the analyzing unit may be able to detect each discrete sweat droplet 1112 being carried thereto by the carrier fluid. Suitable examples of such a carrier fluid include oils that do not absorb moisture, i.e. have relatively low or negligible hygroscopicity, such as oxycyte. Oxycyte is a perfluorocarbon compound, which is commonly used as a blood replacement.

In such an example in which a carrier fluid flow detaches the sweat droplet 1112, a further plate 1128 may be provided opposing the plate 1110 delimiting the chamber 1102, as previously described. The sweat droplet 1112 may form and grow until the sweat droplet 1112 makes contact with the further plate 1128, whereupon the sweat droplet 1112 may block the passage defined by the space between the respective plates 1110, 1128. The sweat droplet 1112 may then be displaced by the flow of carrier fluid. In this manner, relatively uniformly sized sweat droplets 112 may be afforded; their size being determined by the distance 1130 between the plates 1110, 1128. The flow of carrier fluid may further assist in transporting the sweat droplets 112 to the one or more analyzing units.

In cases where, for example, this flow of carrier fluid is insufficient to detach the sweat droplet 1112, the fluid transport assembly may be configured to induce pulses or peaks in the flow rate, which pulses may provide sufficient pressure to release the sweat droplet 1112 from the outlet 1114. A piezoelectric pump may, for instance, be used to induce such peaks in the flow rate of the carrier fluid. This may be straightforwardly achieved by varying the pulse frequency of the pump.

Thus, such a sensor 1100 is configured for receiving sweat from one or more sweat glands and transporting the sweat as discrete sweat droplets 1112 to the one or more analyzing units, which can then be beneficially used for determining the sweat rate or the swat rate per gland with the second discretization method as disclosed herein.

The sensor 1100 could also use the processing aspect of the second discretization method, as was described herein in detail. For this purpose, the sensor 1100 comprises a processor configured to count a number of sweat droplets 1112 sensed by the analyzing units during a time period, and determine time intervals between consecutive sensed sweat droplets 1112 during the time period. The processor also receives a measure of the volume of each of the counted sweat droplets 1112. The processor is further configured to identify, using the time intervals and the measure of the volume of each of the counted sweat droplets 1112, active, i.e. sweat burst, periods of the one or more sweat glands 1108 during which the one or more sweat glands 1108 are excreting sweat, and rest periods of the one or more sweat glands 1108 during which the one or more sweat glands 108 are not excreting sweat. This process of identifying the sweat burst and rest periods of the one or more sweat glands 1108 concomitantly involves assigning the active periods, and the rest periods to the one or more sweat glands 1108.

The processor then determines the number sweat glands 1108 to which the active and rest periods are assigned, and subsequently determines the sweat rate per gland from the number of sweat droplets 1112, the measure of the volume of each of the counted sweat droplets 1112, and the determined number of sweat glands 1108.

The sensor 1100 thus determines the sweat rate per gland by assigning sweat droplets 1112 to particular sweat glands 1108, based on the intermittent sweat excretion behavior of sweat glands 1108. The sensor may also be physically simpler than conventional sweat sensing systems, since the sensor 1100 may transport sweat droplets 1112 from several inlets/chambers to a common analyzing unit.

The above-mentioned embodiments illustrate rather than limit the invention, and those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor. In the device claim enumerating several means, several of these means may be embodied by one and the same item of hardware. Measures recited in mutually different dependent claims may advantageously be used in combination.

The invention claimed is:

1. A sweat sensor for analyzing a user's sweat uptaken from a user's skin, the sensor comprising:
   one or more inlets through which the user's sweat can be uptaken into the sensor, and
   an analyzer configured for analyzing the sweat uptaken by the sensor to determine a sweat parameter, and
   wherein the sensor is configured for controlling a size of an opening of the one or more inlets by changing a cross-sectional area of the opening of the one or more inlets, and/or selecting inlets with a particular size.

2. The sweat sensor according to claim 1,
   wherein the sensor is configured for controlling the size of the opening of the one or more inlets based on the sweat parameter determined by the analyzer.

3. The sweat sensor according to claim 1, the sensor comprising:
   a plurality of inlets for uptaking sweat,
   wherein at least some of the plurality of inlets differ in their opening size, and
   wherein the sensor is configured for selecting inlets with a particular size.

4. The sweat sensor according to claim 1, wherein the analyzer is configured for comparing the determined sweat parameter of the user with a reference setting for the sweat parameter, to control the size of the opening based on a comparison result.

5. The sweat sensor according to claim 1,
   wherein the determined sweat parameter of the user is at least one of a sweat rate of the user, and a number of active sweat glands per inlet.

6. The sweat sensor according to claim 1, wherein the analyzer is configured for comparing a first value of the sweat parameter determined in a first analytical cycle of the sensor with a second value of the sweat parameter determined in a second analytical cycle of the sensor, the second analytical cycle being subsequent to the first analytical cycle, and wherein the sensor is configured for decreasing the size of the opening of the one or more inlets, which the sensor uses for uptaking the sweat and for analyzing the uptaken sweat in a next analytical cycle, if the second value exceeds the first value.

7. The sweat sensor according to claim 1,
wherein the analyzer is configured for determining a sweat rate per gland of the user,
where the analyzer is configured for measuring a concentration of a biomolecule in the uptaken sweat of the user, and
wherein the sensor is configured for estimating a concentration of the biomolecule in blood of the user based on the determined sweat rate per gland and on the measured concentration of the biomolecule in the uptaken sweat.

8. The sweat sensor according to claim 1, further comprising:
a plurality of inlets with a respective opening that is adjustable in size by the sensor,
wherein the sensor is configured for determining from the uptaken sweat a sweat rate of the user and/or a number of active sweat glands of the user, and
wherein the sensor is configured for steering all inlets of the plurality of inlets to the same opening size based on the determined sweat rate and/or the determined number of active sweat glands.

9. The sweat sensor according to claim 1, further comprising:
a flow sensor disposed in a channel of the sensor, which channel connects at least one inlet with the analyzer, and
wherein the flow sensor is configured for measuring an excretion rate of excreted sweat.

10. A method of analyzing a user's sweat uptaken by a sensor from the user's skin through one or more inlets of the sensor, the method comprising the steps:
analyzing at least some of the uptaken sweat, and
controlling, based on a result of the analysis of the uptaken sweat, a size of an opening of the one or more inlets in a subsequent analysis cycle, and
wherein the control of the size is carried out by increasing or decreasing the size of an adjustable opening of the at least one inlet and/or by selecting one or more inlets with a larger opening or with a smaller opening for a next analysis cycle as compared to the size of the opening of the inlets that were used in the previous analysis cycle.

11. The method according to claim 10, the method comprising:
determining a number of active sweat glands per inlet from which the sweat is uptaken by the sensor, and
comparing the determined number of active sweat glands per inlet with a reference setting regarding the number of active sweat glands per inlet,
wherein the control of the size is carried out by one or more of:
increasing the size of the opening of the at least one inlet and/or by selecting one or more inlets with a larger opening for the next analysis cycle as compared to the size of the opening of the one or more inlets that were used in the previous analysis cycle when the determined number of active sweat glands per inlet is below a pre-defined minimum number of active sweat glands per inlet defined in the reference setting, or
decreasing the size of the opening of the at least one inlet and/or by selecting one or more inlets with a smaller opening for the next analysis cycle as compared to the size of the opening of the one or more inlets that were used in the previous analysis cycle when the determined number of active sweat glands per inlet is above a pre-defined maximum number of active sweat glands per inlet defined in the reference setting.

12. The method according to claim 11, comprising:
determining a sweat rate of the user, and
using the determined sweat rate for determining the number of active sweat glands per inlet from which the sweat is uptaken by the sensor.

13. A non-transitory program element for analyzing a user's sweat uptaken by a sensor from the user's skin, which program element, when being executed by a processor, is adapted to carry out the method of claim 10.

* * * * *